US006261571B1

(12) United States Patent
Hovanessian et al.

(10) Patent No.: US 6,261,571 B1
(45) Date of Patent: *Jul. 17, 2001

(54) IMMUNOGENIC COMPOSITIONS COMPRISING DIMERIC FORMS OF THE HUMAN IMMUNODEFICIENCY VIRUS TYPE 2 (HIV-2) AND SIMIAN IMMUNODEFICIENCY VIRUS (SIV) ENVELOPE GLYCOPROTEINS

(75) Inventors: Ara G. Hovanessian, Montreuil; Marie-Anne Rey, Paris; Anne G. Laurent, Paris; Bernard Krust, Paris; Luc Montagnier, Le Plessis-Robinson, all of (FR)

(73) Assignee: Institute Pasteur, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 08/364,829

(22) Filed: Dec. 27, 1994

Related U.S. Application Data

(62) Division of application No. 08/002,756, filed on Jan. 13, 1993, now Pat. No. 5,470,702, which is a division of application No. 07/356,459, filed on May 25, 1989, now Pat. No. 5,208,321, which is a continuation-in-part of application No. 07/204,346, filed on Jun. 9, 1988, now abandoned.

(51) Int. Cl.[7] .................................................. A61K 39/21
(52) U.S. Cl. .................................. 424/208.1; 424/188.1; 530/350; 530/300
(58) Field of Search ............................ 424/160.1, 188.1, 424/208.1; 436/536; 530/388.5, 389.4, 391.3

(56) References Cited

U.S. PATENT DOCUMENTS

| 5,051,496 | * | 9/1991 | Alizon et al. ........................ 530/324 |
| 5,066,782 | * | 11/1991 | Montagnier et al. ................. 530/324 |
| 5,079,342 | * | 1/1992 | Alizon et al. ........................ 530/324 |
| 5,208,321 | * | 5/1993 | Hovanessian et al. .............. 530/350 |
| 5,597,896 | * | 1/1997 | Montagnier et al. ........... 530/388.35 |
| 5,766,844 | | 6/1998 | Sarngadharan et al. ................. 435/5 |
| 5,807,992 | * | 9/1998 | Hovanessian et al. .............. 530/350 |

OTHER PUBLICATIONS

Galfrè et al., 1981, "Preparation of Monoclonal Antibodies: Strategies and Procedures", Meth. Enzymol. 73:3–46.*
Chakrabarti et al., 1987, "Sequence of simian immunodeficiency virus from macaque and its relationship to other human and simian retroviruses", Nature 328:543–547.*
Harlow et al., eds., 1988, Antibodies: A Laboratory Manual, Cold Spring Harbor Laboratory, pp. 100–123.*
Walsh, E. E., et al., 1985, "Purification and characterization of the respiratory syncytial virus fusion protein.", J. Gen. Virol. 66:409–415.*
Rey, M.–A., et al., 1989, "Characterization of an HIV–2–related virus with a smaller sized extracellular envelope glycoprotein.", Virol. 173:258–267.*
Clavel et al., New Engl. J. Med. 316:1180–1185.*
Rey et al., 1990, J. Virol. 64:922–926.*

* cited by examiner

Primary Examiner—Laurie Scheiner
Assistant Examiner—Jeffrey S. Parkin
(74) Attorney, Agent, or Firm—Finnegan, Henderson, Farabow, Garrett & Dunner, L.L.P.

(57) ABSTRACT

The invention relates to an isolated immune complex comprising a protein and an antibody that binds with said protein, wherein the protein is selected from the group consisting of gp80 of HIV-2 and gp65 of SIV, wherein said gp80 is a glycoprotein having an apparent molecular weight of 80 kDa, as determined by SDS-PAGE, and further wherein said gp65 is a glycoprotein having an apparent molecular weight of 65 kDa as determined by SDS-PAGE. Also provided are an immunogenic composition comprising an amount of gp80 protein of human immunodeficiency virus type 2 (HIV-2) sufficient to induce an immune response and a pharmaceutically acceptable carrier, and a composition comprising at least one antigen selected from the group consisting of gp80 protein of HIV-2 and $gp65_{SIV}$.

8 Claims, 11 Drawing Sheets

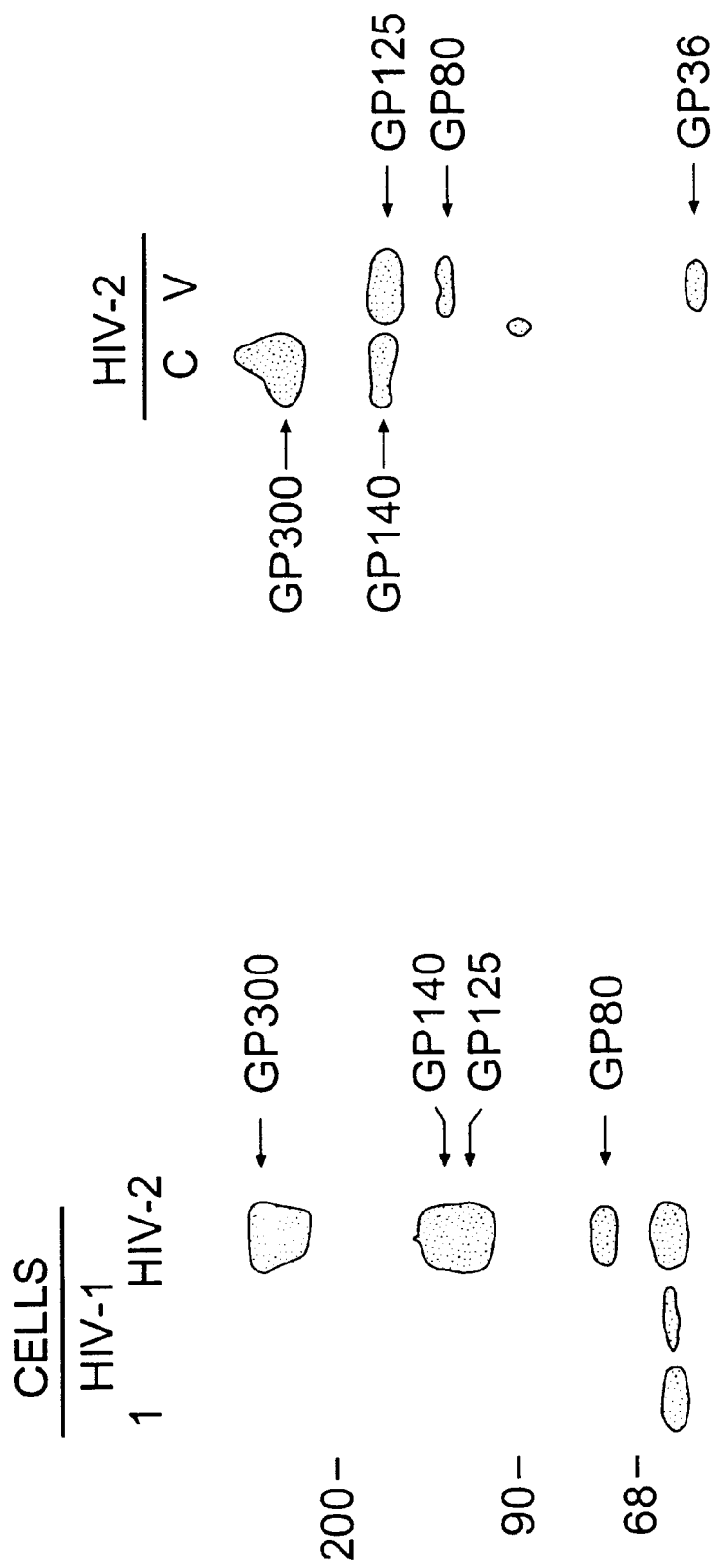

Figures 1A, 1B:
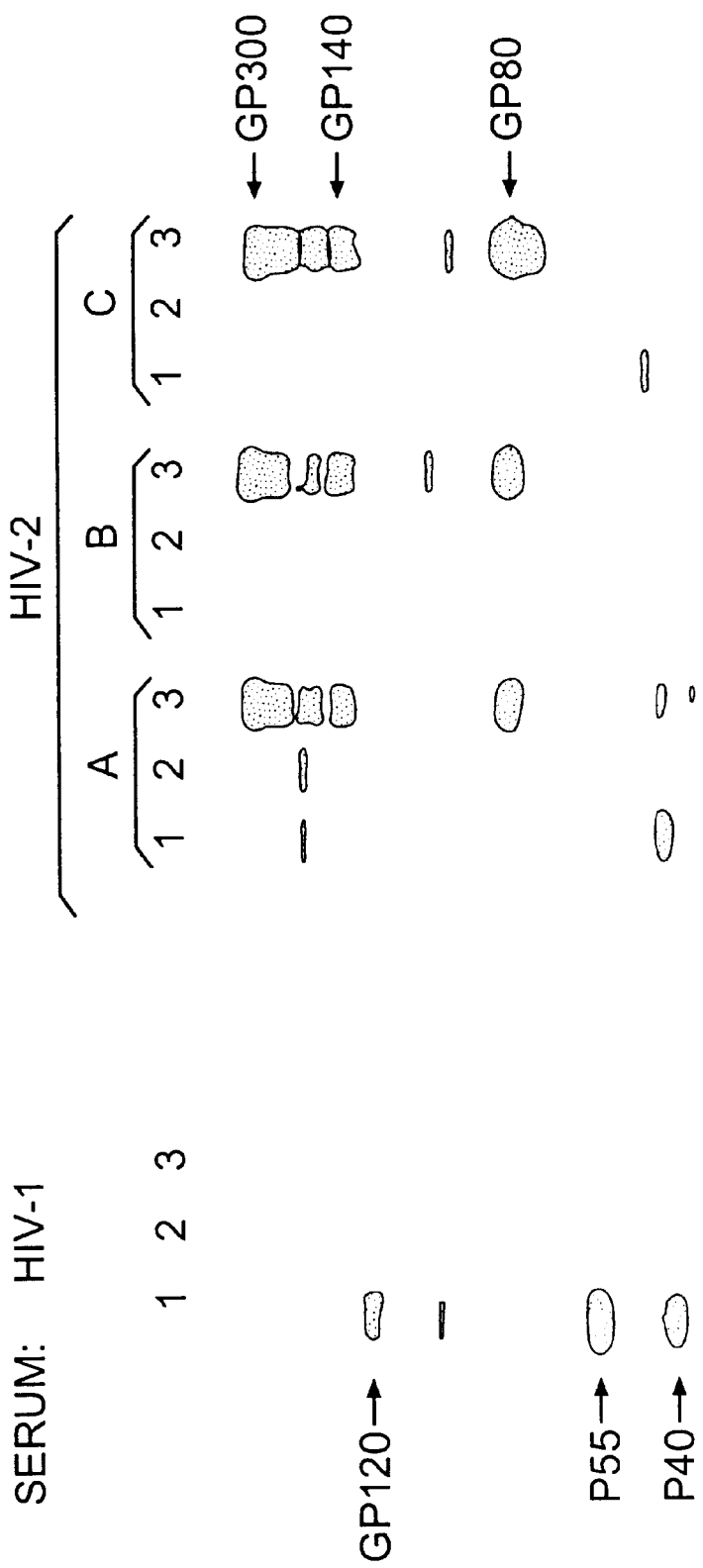

IMMUNOGENIC COMPOSITIONS COMPRISING DIMERIC FORMS OF THE HUMAN IMMUNODEFICIENCY VIRUS TYPE 2 (HIV-2) AND SIMIAN IMMUNODEFICIENCY VIRUS (SIV) ENVELOPE GLYCOPROTEINS

CROSS-REFERENCE TO RELATED APPLICATION

This is a division of application Ser. No. 08/002,756, filed Jan. 13, 1993, now U.S. Pat. No. 5,470,702 which is a division of application Ser. No. 07/356,459, filed May 25, 1989, now U.S. Pat. No. 5,208,321, which is a continuation-in-part of application Ser. No. 07/204,346, filed Jun. 9, 1988, now abandoned.

BACKGROUND OF THE INVENTION

This invention relates to viral proteins and glycoproteins, to compositions containing these proteins, to methods of preparing the proteins, and to their use in detecting viral inection.

Human immunodeficiency virus (HIV) is the etiological agent of acquired immunodeficiency syndrome (AIDS) (Montagnier et al., 1984). To date, two related but distinct viruses HIV-1 and HIV-2, have been identified (Barre-Sinoussi et al., 1983; Brun-Vezinet et al., 1987; Clavel et al., 1986a, 1986b; Guyader et al., 1987; Popovic et al., 1984; Ratner et al., 1985; Wain-Hobson et al., 1985). HIV-2 is closely related to simian immunodeficiency virus (SIV-mac), which causes an AIDS-like disease in macaques (Daniel et al., 1985; Fultz et al., 1986; Chakrabarti et al., 1987). Alignments of the nucleotide sequences of HIV-1, HIV-2, and SIV reveal a considerable homology between HIV-2 and SIV-mac. These two viruses share about 75% overall nucleotide sequence homology, but both of them are only distantly related to HIV-1 with about 40% overall homology (Guyader et al., 1987; Chakrabarti et al., 1977).

In addition to the genes that encode structural proteins (the virion capsid and envelope glycoproteins) and the enzymes required for proviral synthesis and integration common to all retroviruses, HIV-1, HIV-2, and SIV encode genes that regulate virus replication as well as genes that encode proteins of yet unknown function. The only notable difference in the genetic organizations of HIV-1, HIV-2, and SIV resides in the open reading frame referred to as vpx, which is absent in HIV-1 and vpu in HIV-1 but not in HIV-2 and SIV (Cohen et al., 1988; Guyader et al., 1987). These viruses are both tropic and cytopathic for CD4 positive T lymphocytes (Klatzmann et al., 1984; Clavel et al., 1985a; Dalgleish et al., 1984; Daniel et al., 1985). A great number of studies have indicated that CD4 functions as the cellular receptor of HIV (Weiss, 1988).

The HIV-1 env gene encodes a 160-kilodalton (kDa) glycoprotein that is proteolytically cleaved to yield the extracellular and transmembrane proteins, gp120 and gp41, respectively (Montagnier et al., 1985). Similarly, HIV-2 env gene encodes a precursor glycoprotein which is then processed to the mature extracellular and transmembrane glycoproteins (Rey et al., 1989). However, unlike HIV-1, the processing of HIV-2 envelope precursor gp140 seems to require the formation of a homologous dimer (gp300) during its processing. Interestingly, dimerization of the envelope precursor is also observed in SIV infected cells (Rey et al. 1989). Accordingly, dimer formation seems to be a specific property of HIV-2 and SIV envelope gene expression.

There exists a need in the art for additional information on the structure and in vivo processing of HIV-2 proteins, and especially HIV-2 envelope proteins and glycoproteins. Such information would aid in identifying HIV-2 infection in individuals. In addition, such findings could aid in elucidating the mechanism by which HIV-2 infection and virus proliferation occur and thereby make it possible to devise modes of intervening in viral processes.

SUMMARY OF THE INVENTION

This invention aids in fulfilling these needs in the art by providing HIV-2 envelope proteins and glycoproteins in purified form. More particularly, this invention relates to the processing of HIV-2 envelope glycoproteins and the characterization of the transmembrane glycoprotein. Previously, the detection of the transmembrane glycoprotein had been handicapped by the lack of specific antibodies. For this reason, polyclonal antibodies were prepared against the purified HIV-2 envelope precursor. Furthermore, monoclonal antibodies were prepared against a synthetic polypeptide deduced from the sequence of the transmembrane glycoprotein of HIV-2. With the help of these antibodies the membrane glycoproteins of HIV-2 and SIV were identified.

It was discovered that the transmembrane proteins exist as a homodimer in the infected cells as well as in the virions. Dimeric forms of the transmembrane giycoproteins of HIV-2 and SIV can be dissociated in an ionic detergent to 36 kDa and 32 kDa proteins, respectively. Conformational modifications brought about by the formation of envelope precursor might be necessary for transport of the glycoprotein precursor to the Golgi apparatus and its processing into the mature glycoprotein products, the extracellular and transmembrane envelope proteins. Furthermore, the transmembrane dimer might be essential for optimal structure of the virion and thus its infectivity.

This invention thus provides gp80 structural glycoprotein of HIV-2 dimeric form of the transmembrane glycoprotein and human retroviral variants of HIV-2 containing the structural glycoprotein in purified form.

A similar high molecular weight glycoprotein of Simian Immunodeficiency Virus (SIV) or of a Simian retroviral variant of SIV has also been discovered. This glycoprotein is the dimeric form of transmembrane glycoprotein of SIV and has an apparent molecular weight of about 65 kDa ($gp65_{SIV}$). This glycoprotein is also provided in a purified form.

This invention also provides labeled gp80 of HIV-2 and gp65 of SIV. Preferably, the labeled glycoproteins are in purified form. It is also preferred that the labeled glycoprotein is capable of being immunologically recognized by human body fluid containing antibodies to HIV-2 or SIV. The glycoproteins can be labeled, for example, with an immunoassay label selected from the group consisting of radioactive, enzymatic, fluorescent, chemiluminescent labels, and chromophores.

Immunological complexes between the proteins and glycoproteins of the invention and antibodies recognizing the proteins and giycoproteins are also provided. The immunological complexes can be labeled with an immunoassay label selected from the group consisting of radioactive, enzymatic, fluorescent, chemiluminescent labels, and chromophores.

Furthermore, this invention provides a method for detecting infection of cells by human immunodeficiency virus type-2 (HIV-2). The method comprises providing a composition comprising cells suspected of being infected with HIV-2, disrupting cells in the composition to expose intracellular proteins, and assaying the exposed intracellular proteins for the presence of gp80 glycoprotein of HIV-2. The exposed intracellular proteins are typically assayed by electrophoresis or by immunoassay with antibodies that are immunologically reactive with gp80 glycoprotein of HIV-2.

This invention provides still another method of detecting antigens of HIV-2, which comprises providing a composition suspected of containing antigens of HIV-2, and assaying the composition for the presence of gp80 glycoprotein of HIV-2. The composition is typically free of cellular debris. The molecular weight of the gp80 is estimated more or less 10%. The same for the other molecular weight mentioned in the present invention.

A method of distinguishing HIV-2 infection from HIV-1 infection in cells suspected of being infected therewith has also been discovered. The method comprises providing an extract containig intracellular proteins of the cells, and assaying the extract or the presence of gp80 glycoprotein. The gp80 is characteristic or HIV-2, but the glycoprotein has not been found in extracts of HIV-1 cell cultures.

In addition, this invention provides a method of making gp80 glycoprotein of HIV-2, which comprises providing a composition containing cells in which HIV-2 is capable of replicating, infecting the cells with HIV-2, and culturing the cells under conditions to cause HIV-2 to proliferate. The cells are then disrupted to expose intracellular proteins. The gp80 glycoprotein is recovered from the resulting exposed intracellular proteins. It could be also recovered by detergent solubilization of HIV-2 virions.

This invention also provides an in vitro diagnostic method for the detection of the presence or absence of antibodies which bind to an antigen comprising the proteins or glycoproteins of the invention or mixtures of the proteins and glycoproteins. The method comprises contacting the antigen with a biological fluid for a time and under conditions sufficent for the antigen and antibodies in the biological fluid to form an antigen-antibody complex, and then detecting the formation of the complex. The detecting step can further comprise measuring the formation of the antigen-antibody complex. The formation of the antigen-antibody-complex is preferably measured by immunoassay based on Western Blot technique, ELISA (enzyme linked immunosorbent assay), indirect immunofluorescent assay, or immunoprecipitation assay.

A diagnostic kit for the detection of the presence or absence of antibodies which bind to the proteins or glycoproteins of the invention or mixtures of the proteins and glycoproteins contains antigen comprising the proteins, glycoproteins, or mixtures thereof and means for detecting the formation of immune complex between the antigen and antibodies. The antigens and the means are present in an amount sufficient to perform the detection.

This invention provides a method of preparing envelope transmembrane glycoproteins, which comprises providing an extracellular composition containing gp80 glycoprotein of HIV-2 or gp65 of SIV and then dissociating the glycoprotein of HIV-2 or the glycoprotein of SIV. A nonglycosylated dimeric form of the transmembrane envelope protein of HIV-2 (and SIV) can be obtained from the glycosylated form of gp80 (or gp65) by using specific enzymes (i.e. endo F), which cleave mature oligosaccharide chains. Another procedure for the production of unglycosylated forms of such dimeric protein could be genetic engineering methods (see Reference 16).

This invention also provides an immunogenic composition comprising a protein or glycoprotein of the invention in an amount sufficient to induce an immunogenic or protective response in vivo, in association with a pharmaceutically acceptable carrier therefor. A vaccine composition of the invention comprises a utralizing amount of the dimeric transmembrane envelope glycoprotein or unglycosylated form thereof and a pharmaceutically acceptable carrier therefor.

The dimeric form of the transmembrane glycoprotein is highly recognized by all sera positive for HIV-2 antigens. Therefore, the detection of gp80 could be used as a marker for characterization of HIV-2 positive sera and for differentiation from HIV-1 positive sera.

The proteins and glycoprotein of this invention are thus useful as a portion of a diagnostic composition for detecting the presence of antibodies to antigenic proteins associated with HIV-2 and SIV. In addition, the proteins and glycoproteins can be used to raise antibodies for detecting the presence of antigenic proteins associated with HIV-2 and SIV. The proteins and glycoproteins of the invention can be also employed to raise neutralizing antibodies that either inactivate the virus, reduce the viability of the virus in vivo, or inhibit or prevent viral replication. The ability to elicit virus-neutralizing antibodies is especially important when the proteins and glycoproteins of the invention are used in vaccinating compositions.

BRIEF DESCRIPTION OF THE DRAWINGS

This invention will be described in greater detail by referring to the drawings in which:

FIG. 1 is an autoradiograph of a specific 80-kDa protein in HIV-2 infected cells. Western blot analysis was made using an HIV-1 positive serum and 3 HIV-2 positive sera (A, B and C). Extracts (material from $10^6$ cells) from control uninfected (lanes 2), HIV-1 infected (lanes 1), and HIV-2 infected (lanes 3) CEM cells were analyzed by polyacrylamide gel (7.5%) electrophoresis before the Western blot assay. On the left, the arrows indicate the position of HIV-1 extracellular glycoprotein (gp120) and gaq precursors p55 and p40. On the right is the position of HIV-2 specific gp300, gp140, and gp80 .

FIG. 2 is a fluorograph relating to synthesis of HIV-2 related glycoproteins. HIV-2 infected cells were labeled with [$^3$H] glucosamine (200 $\mu$Ci/ml; $4\times10^6$ cells/ml) for 2, 3, 4, 6, and 8 hr. At different points, extracts (material from $10^7$ cells) were prepared from infected cells and from the virus pellet (prepared by 100,000 g centrifugation of the culture medium). Aliquots from these extracts (corresponding to $2\times10^6$ cells) were purified on HIV-2 serum-Sepharose, and the labeled proteins were analyzed by polyacrylamide gel (12.5%) electrophoresis. On the left is the position of protein mol. wt. markers: myosin, 200,000; phosphorylase B, 97,000; bovine serum albumin, 68,000; ovalbumin, 43,000; carbonic anhydrase, 30,000.

FIG. 3 depicts a Western blot analysis with polyclonal antibodies against gp300. On the left, extracts from uninfected (–) and HIV-1 or HIV-2 infected CEM cells are shown. On the right, extracts from HIV-2 infected CEM cells are shown: cell extracts (lane C) and virus pellet (lane V). These samples were analyzed by polyacrylamide gel electrophoresis (7.5% gel on the left; 12.5% gel on the right) before Western blot analysis using murine polyclonal antibodies raised against the purified gp300 (anti-gp300). An autoradiogram is shown. Each sample corresponded to material from $10^6$ cells.

FIG. 4 depicts a Western blot analysis using the monoclonal antibody mAb 1H8. Extracts from HIV-1 or HIV-2 infected cells (lanes C) and virus pellet (lanes V) were analyzed by polyacrylamide gel (12.5%) electrophoresis before Western blot assay using mAb 1H8. An autoradiograph is shown. This monoclonal antibody was raised against synthetic peptide p39' of the purified HIV-2 virus and it is directed against the transmembrane glycoprotein of HIV-2 envelope.

Figure 5:
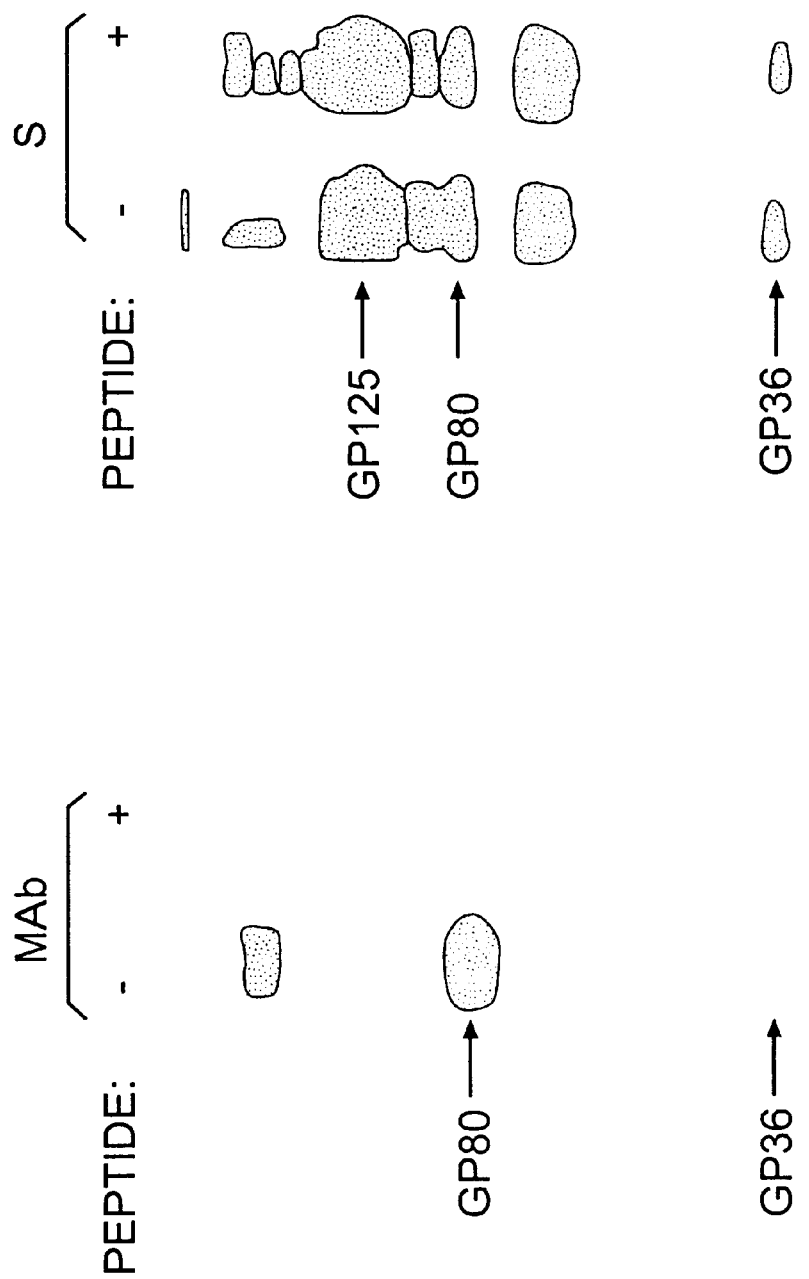

FIG. 5 shows that peptide p39' blocks the binding of mAb 1H8 to gp80. Extracts from the HIV-2 virus pellets were analyzed by Western blot assay using mAb 1H8 (section mAb) or anti-gp300 polyclonal antibodies (section S). Incubation with each antibody was carried out in the absence (lanes−) or presence (lanes+) of 10 μg of peptide p39'. The results of the autoradiography are shown.

Figure 6:
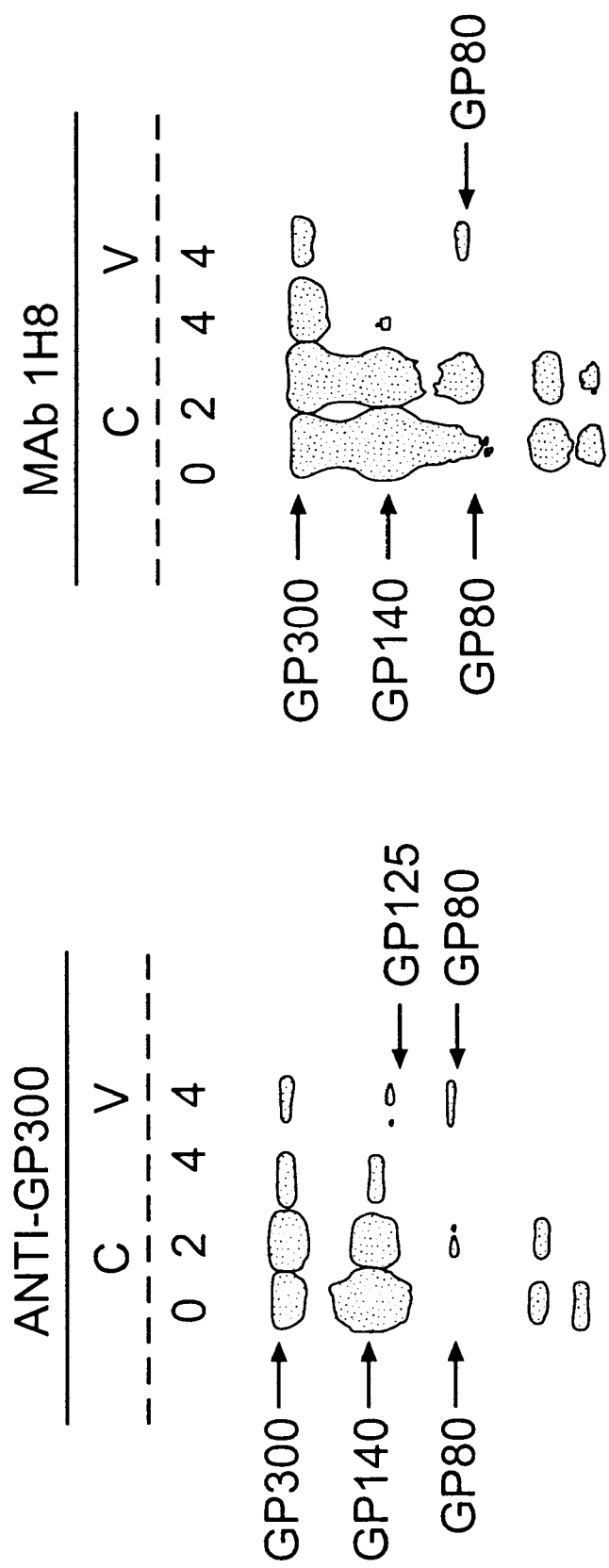

FIG. 6 depicts the results of pulse chase experiments to show the production of gp80 in HIV-2 infected cells. HIV-2 infected CEM cells were labeled with [$^{35}$S] methionine (200 μCi/ml; 4×10$^6$ cells/ml) for 2 hr (lanes 0). The radioactive label was then chased in culture medium containing 5 mM cold methionine for 2 and 4 hr (lanes 2 and 4). The culture medium at 4 hr was centrifuged at 100,000 g and the pellet was extracted. All samples were immunoprecipitated using anti-gp300 or mAb 1H8 antibodies. The labeled proteins in the immune complex preparations were eluted in the electrophoresis sample buffer and analyzed by plyacrylamide gel (7.5%) electrophoresis. A fluorograph is shown. C and V stand for cell and virus extracts, respectively. Each sample represents material from 10$^6$ cells.

Figure 7:
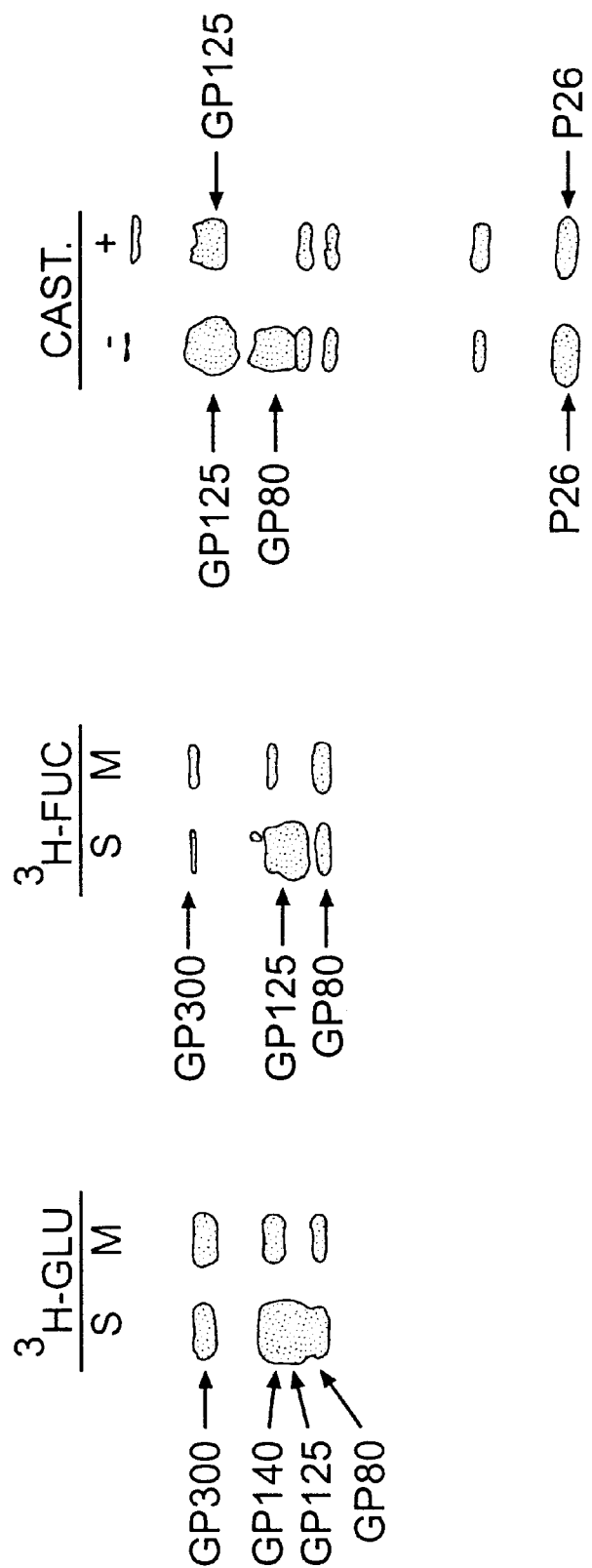

FIG. 7 shows (a) incorporation of labeled glucosamine and fucose into gp80; and (b) the effect of castanospermine on the production of gp125 and gp80. (a) HIV-2 infected CEM cells labeled with [$^3$H] glucosamine (200 μCi/ml or with [$^3$H] fucose (200 μCi/ml) were assayed by immunoprecipitation using anti-gp300 polyclonal antibodies (lanes S) or the monoclonal antibody mAb 1H8 (lanes M). All samples were analyzed by polyacrylamide gel (12.5%) electrophoresis. A fluorograph is shown. (b) HIV-2 infected cells were labeled (16 hr) with [$^{35}$S] methionine (200 μCi/ml; 4×10$^6$ cells/ml) in the absence (lane−) or presence (lanes+) of castanospermine (1 mM). Extracts from the culture medium containing virus particles were purified by immunoaffinity column using HIV-2 serum-Sepharose, and the purified proteins were assayed by polyacrylamide gel (12.5%) electrophoresis. A fluorograph is shown.

Figure 8:
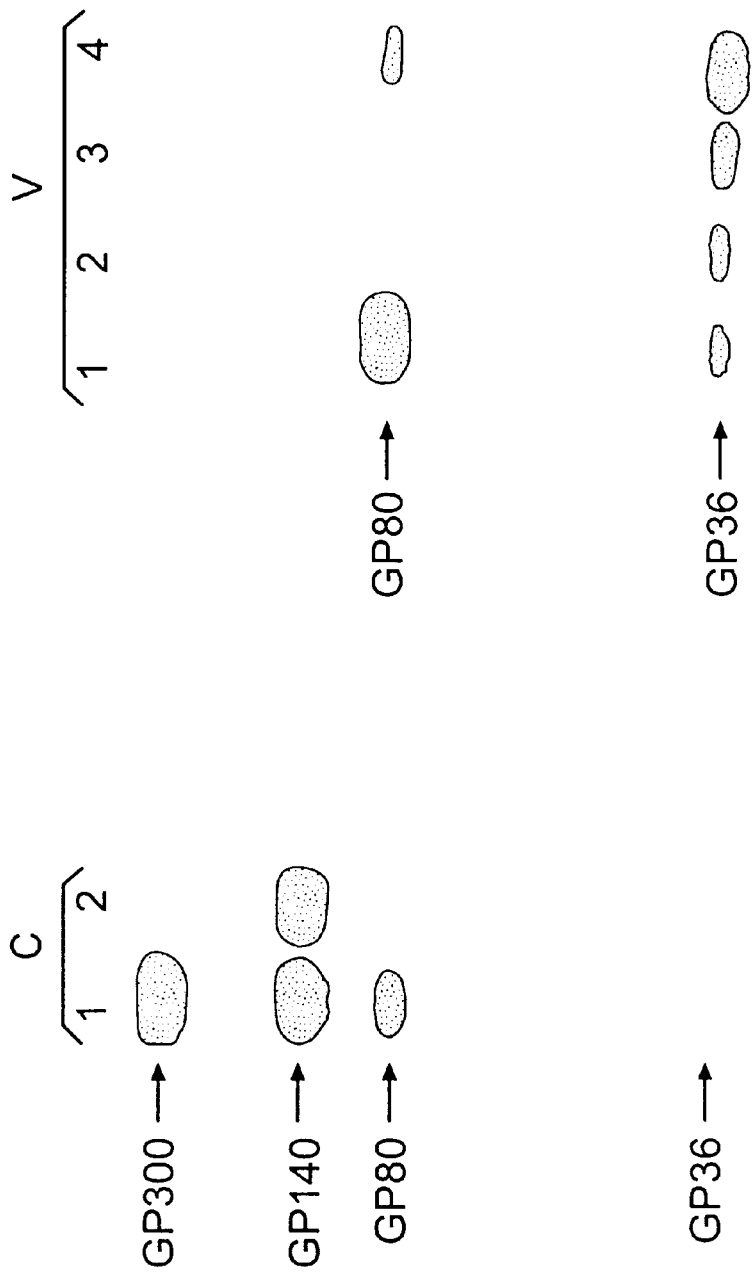

FIG. 8 relates to dissociation of gp80. Section C; extracts from [$^{35}$S] methionine labeled, HIV-2 infected CEM cells were assayed by immunoprecipitation using the monoclonal antibody mAb 1H8 (lane 1). Another aliquot of the same cell extract preparation was first heated (95° C., 5 min) in the presence of 1% SDS, then it was diluted 10 fold in RIPA buffer before the immunoprecipitation assay (lane 2). The immune complex preparations were analyzed by electrophoresis. Each sample was from extracts corresponding 10$^6$ cells. Section V: HIV-2 virus pellets from [$^{35}$S] methionine labeled cells (each corresponding to material from 10$^7$ cells) were suspended in different buffers: (1) lysis buffer containing Triton (10 mM Tris-HCl pH 7.6, 150 mM NaCl, 1 mM EDTA, 1% (v/v) Triton X-100, 100 units/ml aprotinin); (2) lysis buffer containing SDS (as in 1, but containing 1% (v/v) SDS instead Triton X-100); (3) lysis buffer containing SDS and then heated (95° C., 5 min); (4) RIPA buffer (as in 1, but also containing 0.1% (v/v) SDS and 0.2% (v/v) deoxycholate). All these samples were then immunoprecipitated using mAb 1H8 and labeled proteins were analyzed by polyacrylamide gel (12.5%) electrophoresis. A fluorograph is shown.

Figure 9:
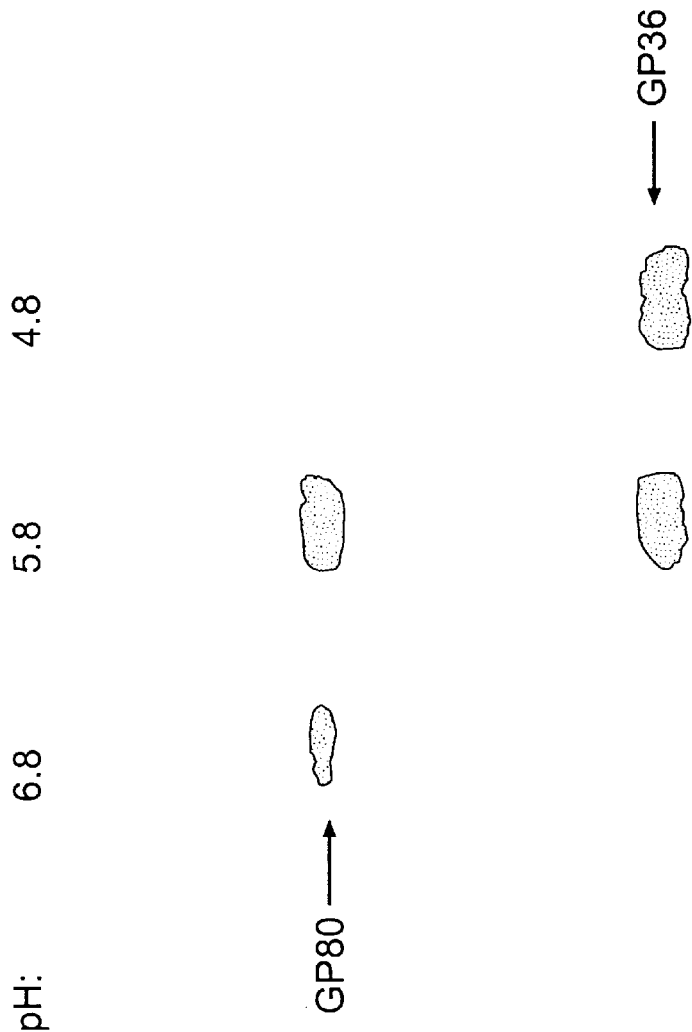

FIG. 9 relates to dissociation of the purified gp80 into gp36. HIV-2 infected CEM cells were labeled (17 hr) with [$^{35}$S] methionine and the virus pellets were suspended is lysis buffer containing Triton. These virus extracts (material corresponding from 2×10$^7$ cells) were immunoprecipitated using mAb 1H8, and gp80 was purified by preparative gel electrophoresis. Equal aliquots of the purified gp80 preparation were lyophilized and suspended in 100 mM acetate at pH 6.8, 5.8, and 4.8 containing 1% (v/v) SDS, 100 units/ml aprotinin and 5 mM EGTA (to inhibit calcium-dependent proteolysis). All the samples were incubated at 30° C. for 50 min before dilution in 2 fold concentrated electrophoresis buffer. Samples were analyzed by polyacrylamide gel (12.5%) electrophoresis. A fluorograph is shown.

Figures 10A, 10B:
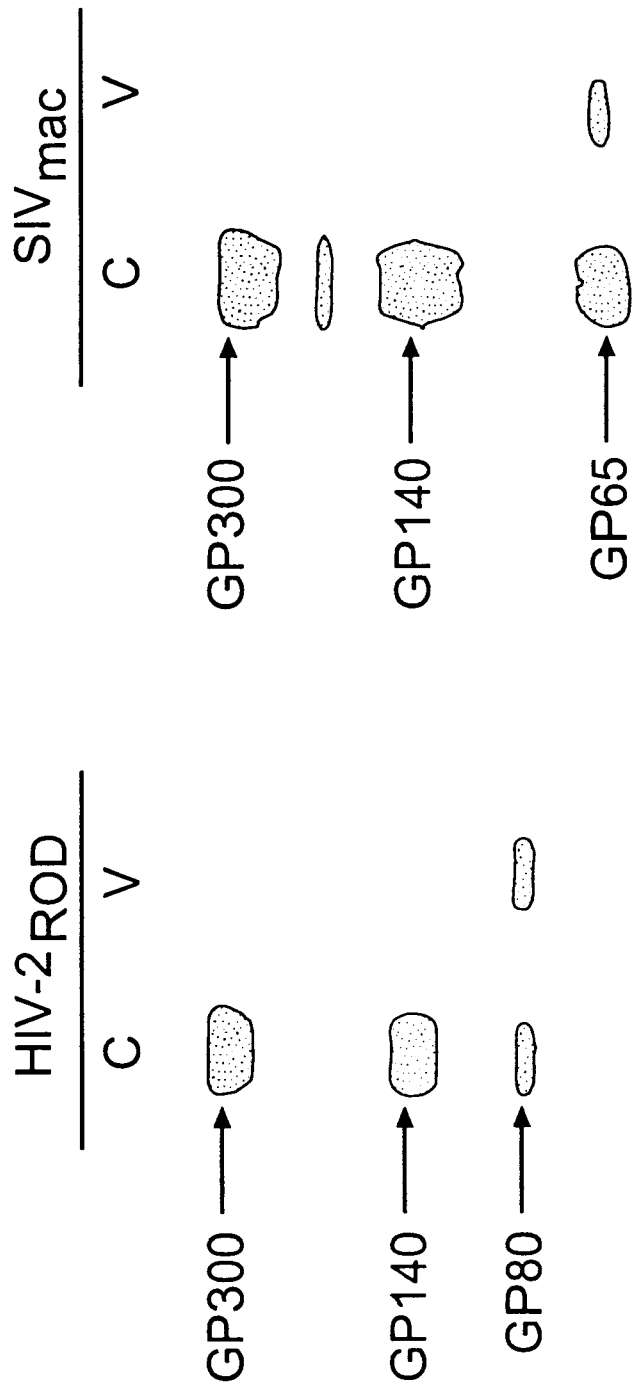

FIG. 10 substantiates that the transmembrane glycoprotein of SIV exists as a dimer. Section Cell: SIV-mac infected HUT-78 cells and HIV-2 infected CEM cells were labeled for 16 hr with [$^3$H] glucosamine (200 μCi/ml; 4×10$^6$ cells/ml). Extracts (prepared in lysis buffer containing Triton) from infected cells were purified by immunoprecipitation using mAb 1H8 and the labeled proteins were analyzed by polyacrylamide gel (12.5%) electrophoresis. A fluorograph is shown.

Figure 11:
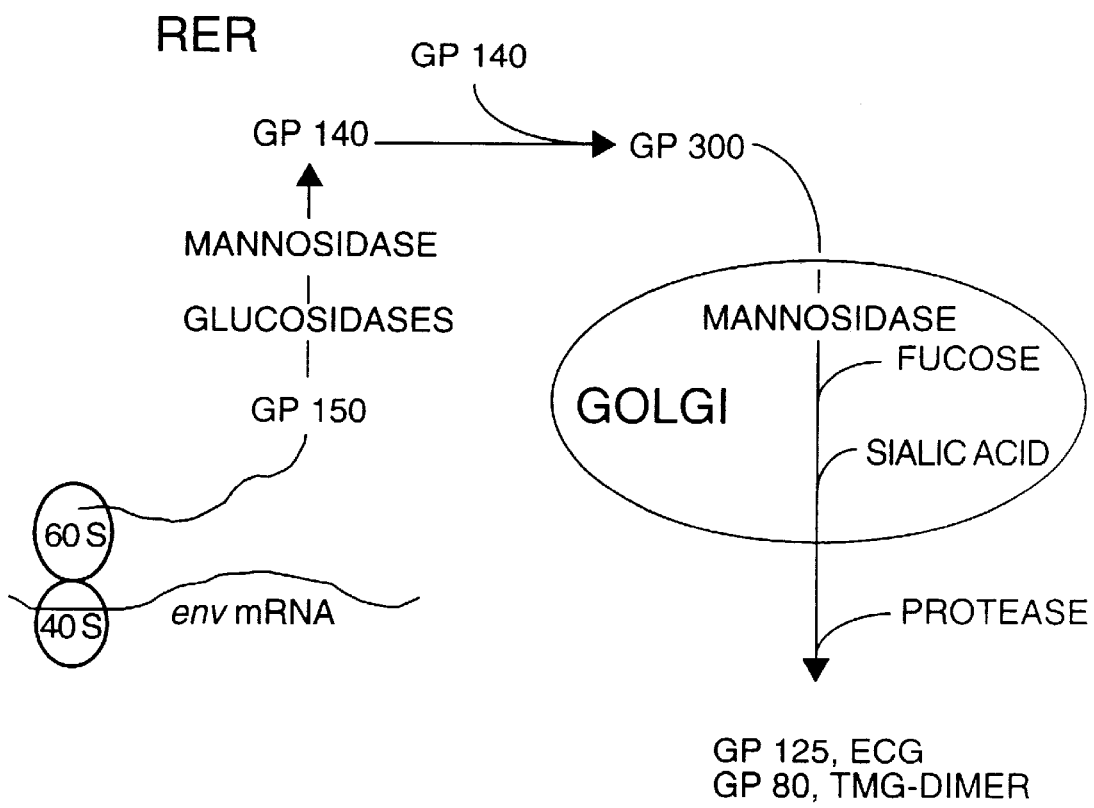

FIG. 11 is a schematic pathway of HIV-2 envelope glycoprotein processing.

DETAILED DESCRIPTION OF PREFERRED EMBODIMENTS

As a result of this invention, the processing of HIV-2 envelope glycoproteins has now been characterized. An 80-Mr glycoprotein (gp80) was produced in HIV-2 infected cells along with three other glycoproteins that were recently reported: the extracellular glycoprotein (gp125), the envelope glycoprotein precursor (gp140), and the transient dimeric form of gp140 (gp300).

The gp125 and gp80 were detectable after the synthesis of gp14 and the formation of gp300. Among these four glycoproteins, only gp80 and gp125 were associated with HIV-2 virions. As the other glycoproteins, gp80 was recognized by all HIV-2 positive sera. A murine polyclonal antibody raised against purified gp300 recognized all four glycoproteins. On the other hand, a monoclonal antibody specific for transmembrane glycoprotein of HIV-2 recognized gp140, gp300, and gp80, thus indicating that gp80 should be related to the transmembrane pro tein of the envelope. Heating (95° C., 5 min) of cellular or viral extracts in 1% SDS resulted in the dissociation of gp80 into the monomer gp36. These results suggest that during the processing of the HIV-2 envelope glycoprotein, the dimeric form of the precursor becomes cleaved by the cellular protease to give the extracellular glycoprotein gp125 and the transmembrane glycoprotein dimer gp80.

Dimerization of envelope glycoprotein precursor and the transmembrane glycoprotein was also observed in cells infected with simian immunodeficiency virus (SIV), a virus closely related to HIV-2. Dimerization of the envelope precursor might be required for its processing to give the mature envelope proteins, whereas the transmembrane dimer might be essential for optimal structure of the virion.

The results obtained in practicing this invention will now be described in greater detail.

I. Detection of a 80 kDa Protein in HIV-2 Infected Cells and in the Virion

Recently, we reported that the precursor of HIV-2 envelope glycoproteins is a 140-kDa protein (gp140), which requires the formation of a homologous dimer during its processing into the mature products, the extracellular (gp125) and transmembrane (gp36) glycoproteins (Rey et al., 1989). In these studies, however, the level of gp36 was found to be very low and in some experiments it was not detectable. It has now been discovered that, in fact, that is the case because the transmembrane glycoprotein exists as a homodimer with an electrophoretic mobility in polyacrylamide gels at a position corresponding to a 80-kDa protein (FIGS. 1 to 6). Accordingly for convenience, this 80-kDa protein will be referred to as gp80.

Crude extracts from uninfected or HIV-1$_{BRU}$ and HIV-2$_{ROD}$ infected CEM cells were analyzed by an electrophoretic transfer immunoblotting assay (Western blot) using an HIV-1 positive serum and three different HIV-2 positive sera from AIDS patients (FIG. 1). The HIV-2 specific sera identified the envelope precursors (gp140 and gp300) and in addition recognized strongly the 80-kDa protein (gp80). These sera were specific for HIV-2 proteins since they did not recognize HIV-1 proteins which were detectable using HIV-1 specific serum: the envelope glycoprotein precursor (gp160) and gag precursors (p55 and p40). The relation of gp80 to HIV-2 infection was demonstrated by several results in which gp80 was not identified by HIV-1 positive serum nor was it found in HIV-1 infected cells.

Western blot analysis of viral pellets prepared by centrifugation (100,000 g for 30 min) of infected culture medium indicated that gp80 was also detectable in HIV-2 particles with the extracellular glycoprotein, gp125 (see below).

II. Synthesis of gp80 in HIV-2 Infected Cells

Figures 2A, 2B:
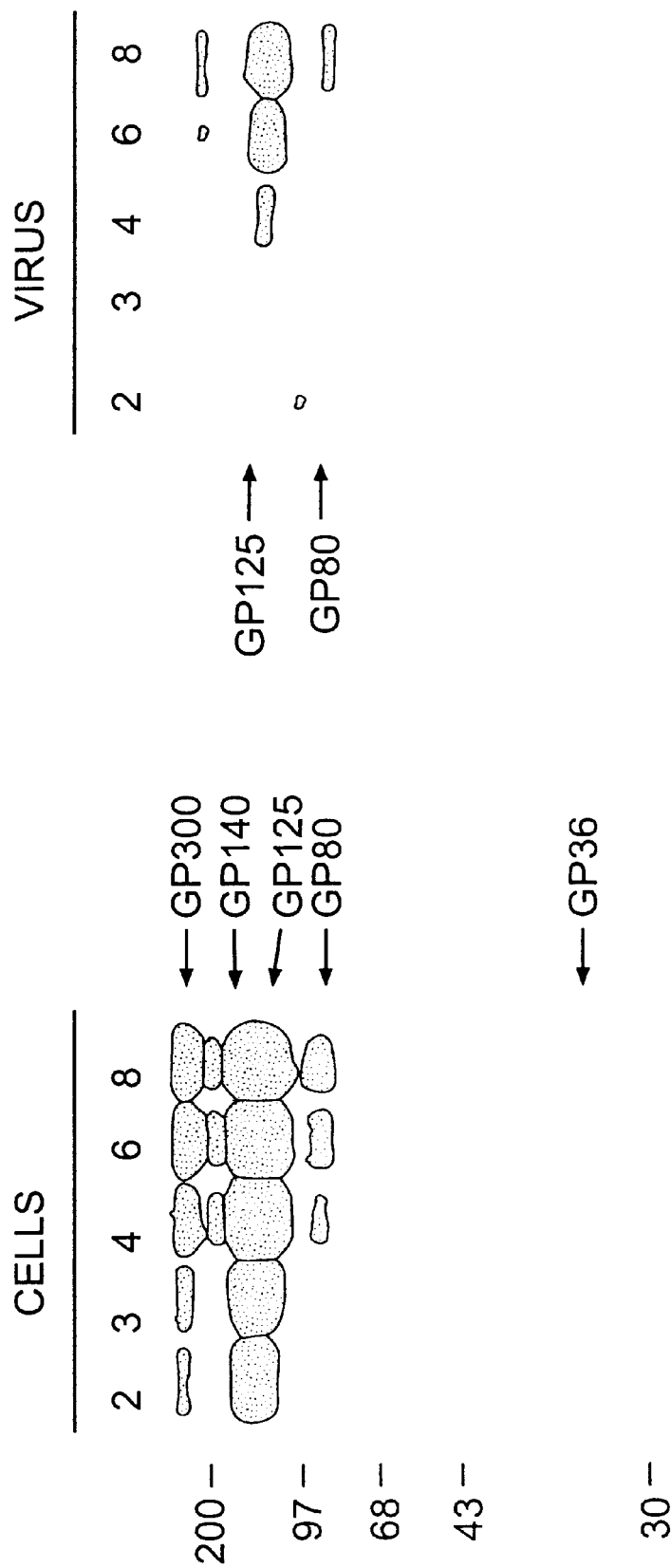

Preliminary experiments indicated that all HIV-2 positive sera can immunoprecipitate gp80 in addition to the envelope precursors gp140 and gp300 and the extracellular glycoprotein, gp125. In order to characterize the synthesis of gp80, an HIV-2 positive serum which recognizes mainly the envelope proteins was used. Purified antibodies from this serum were coupled to CNBr activated Sepharose (HIV-2 serum-Sepharose) and was used as an immunoaffinity column to purify envelope glycoproteins. HIV-2 infected cells were labeled with [$^3$H] glucosamine, and at different times (2, 3, 4, 6, and 8 hr) extracts were prepared from infected cells as well as from virus pellets. All samples were purified on HIV-2 serum-Sepharose and labeled proteins were analyzed by polyacrylamide gel electrophoresis (FIG. 2). At 2 hr, gp140 and gp300 were the only labeled proteins detectable in infected cells; gp125 and gp80 became detectable 3 to 4 hr after the start of the labeling during which time they became also detectable in virus pellets prepared from the culture medium. At 6 to 8 hours after the start of labeling, gp125 and gp80 became clearly detectable. These results indicate, therefore, that gp80 is associated with virus particles and suggest that gp80 might be a mature product of a precursor which requires processing. In these experiment, we could also detect some [$3_H$] glucosamine labeled gp36, but only intracellularly. The identity of the labeled 200 kDa protein is not known (FIG. 2). It is probably a cellular protein since it was not immunoprecipitated by other HIV-2 positive sera.

These kinetics results for the synthesis of HIV-2 envelope glycoproteins are in accord with previous results. In HIV-2 infected cells, gp140 is the first envelope product detectable at 15 min after a pulse-labeling. During a period of chase, the dimeric form of the envelope precursor (gp300) becomes detectable at 0.5 hr, whereas the mature extracellular glycoprotein (gp125) becomes detectable at 1.5 to 3 hr (Rey et al., 1989).

III. Identification of gp80 by Polyclonal Antibodies Against HIV-2 Envelope Precursor In order to characterize HIV-2 envelope glycoproteins, polyclonal antibodies against the purified dimeric precursor, gp300, were prepared. For this purpose, gp300 was first partially purified by an immunoadsorbent with antibodies from HIV-2 seropositive patient serum before purification by preparative electrophoresis. Five mice were immunized with 5 μg of this purified gp300 preparation administered intraperitoneally five times at 10 days interval. Poly(A)·poly (U) (200 μg) were used as an adjuvant which was administered mixed with the antigen (Materials and Methods), infra (see page 36). All mice developed antibodies against gp300. These antibodies are referred to as anti-gp300 polyclonal antibodies.

FIG. 3 shows a Western blot analysis using antibodies from one of the immunized mice. Anti-gp300 antibodies reacted specifically with gp300, but also with gp140, gp125, and gp80 present in HIV-2 infected cells. No specific signal was observed in uninfected or HIV-1 infected CEM cells. The labeling of a 60 kDa protein with anti-gp300 antibodies was probably not specific since it was observed in cell extracts irrespective of virus infection (FIG. 3, section Cells) and in some experiments it was not at all observed.

These polyclonal antibodies were also used in a similar Western blot assay using extracts from HIV-2 infected cells as well as from the virus pellet. In the cellular extracts, the antibodies recognized gp300, gp140, and gp80 (FIG. 3, section HIV-2 lane C). In the viral extracts, they recognized gp125, gp80, and a 36 kDa protein which is probably the transmembrane glycoprotein, gp36 (FIG. 3, section HIV-2 lane V). On prolonged exposures, it was also possible to see a signal at the position of gp36 in cellular extracts (data not shown). It is interesting here to note that the level of gp80 and gp36 was much higher in the viral pellet compared to the cellular extract.

These results indicate that polyclonal antibodies raised against the envelope precursor identify gp80 along with all the components of HIV-2 envelope. Thus, gp80 should be related to HIV-2 envelope. The fact that gp80 is associated with the virus suggests that it is a mature product.

IV. Identification of gp80 by the Monoclonal Antibody 1H8 Specific for the Transmembrane Glycoprotein of HIV-2

Figure 4:
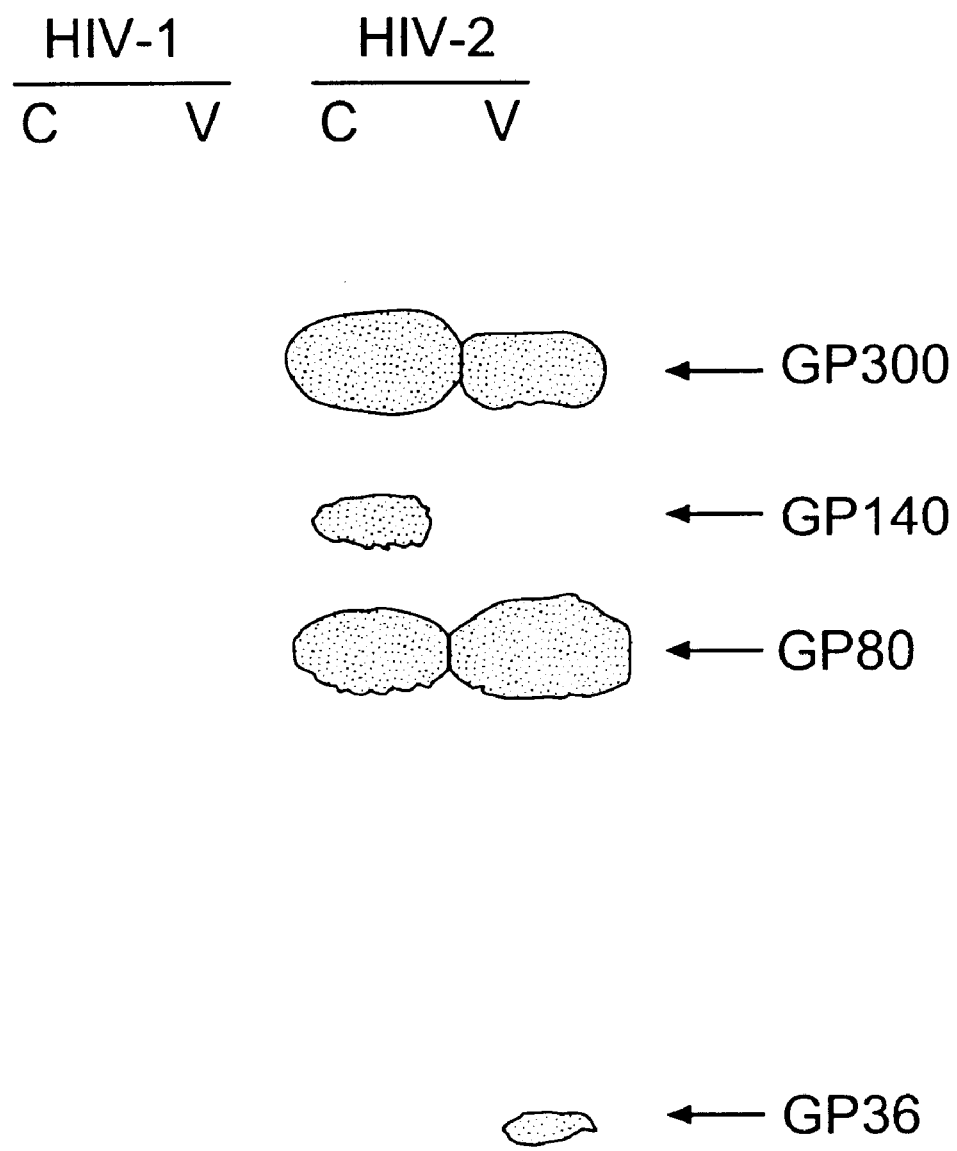

The monoclonal antibody (mAb 1H8) was used in a Western blot assay to determine whether viral proteins can be identified. In HIV-2 infected cells, mAb 1H8 identified gp300, gp140, and gp80, whereas in the HIV-2 pellet it identified mainly gp80 and weakly gp36 and gp300 (FIG. 4). The presence of low levels of gp300 in the virus pellet was probably due to some contamination from lysed cells, since it is a cellular protein (Rey et al., 1989). The weak signal with gp36 probably reflects low levels of this protein. The mAb 1H8 did not recognize proteins in extracts from HIV-1 infected cells or from the virus pellet. Furthermore, it did not recognize the extracellular glycoprotein gp125 (FIG. 4). These results illustrate, therefore, the specificity of mAb 1H8 for HIV-2 envelope precursors (gp140 and gp300) and the transmembrane glycoprotein (gp36). The reactivity of mAb 1H8 was mapped to the amino acid sequence 579–604 within the HIV-2 transmembrane glycoprotein using a synthetic peptide referred to as p39'.

To show the specificity of mAb 1H8 reactivity with gp80, a western blot assay using extracts from HIV-2 virus pellet was carried out. After the transfer of proteins, nitrocellulose sheets were incubated with mAb 1H8 or anti-gp300 polyclonal antibodies in the absence or presence of 1 μg/ml of peptide p39' (FIG. 5). The mAb 1H8 gave a strong signal for gp80. In addition, a signal for gp36 was observed, but only after a prolonged exposure of the autoradiogram. Anti-gp300 polyclonal antibodies reacted with gp125, gp80, and gp36; the 60-kDa signal was not specific (as in FIG. 3).

Addition of peptide p39' completely abolished the signals obtained with mAb 1H8, but not those obtained with anti-gp300 antibodies (FIG. 5). These observations confirm that the reactivity of mAb 1H8 should be with the 26 amino acid residue corresponding to the amino acids 579 to 604 in the transmembrane glycoprotein of HIV-2. Consequently, a seauence corresponding to that of peptide p39' should be present in gp80. The reactivity of anti-gp300 antibodies was not modified by peptide p39'. Therefore, these antibodies should interact with other epitopes than that corresponding to peptide 39'.

V. Immunoprecipitation of gp80 by Anti-gp300 Polyclonal Antibodies and by mAb 1H8

Anti-gp300 polyclonal antibodies immunoprecipitate gp300, gp140, gp125, and gp80, whereas mAb 1H8 immunoprecipitate gp300, gp140, and gp80 (FIG. 6). Two cellular proteins (60 and 45 kDa) were also associated with the immune complex preparations using both polyclonal and monoclonal antibodies (FIG. 6, lanes 0 and 2 hr). The presence of these 60 and 45 kDa proteins in the immune complex preparation was due to their binding to protein A Sepharose. This latter was used in order to recover immune complexes formed with the different antibodies.

HIV-2 infected cells were pulse-labeled for 1 hr before a chase of 2 and 4 hr. Extracts from labeled cells (time 0, 2, and 4 hr) and the viral pellet recovered at 4 hr of chase were analyzed by immunoprecipitation assay using anti-gp300 polyclonal antibodies and mAb 1H8 (FIG. 6). With both polyclonal and monoclonal antibodies, gp80 was not detectable at the period of pulse-labeling. It became clearly apparent at 2 hr of chase in infected cells. When the chase was prolonged to 4 hr, then [$^{35}$S] methionine labeled gp80 became undetectable in infected cells. Analysis of viral pellets produced at 4 hr, indicated that as the extracellular glycoprotein (gp125), gp80 was associated with the virus particles (FIG. 6). These results suggest that gp80 is a product of the processing of HIV-2 envelope. The fact that gp80 was identified by monoclonal antibodies specific for the HIV-2 transmembrane glycoprotein indicated that it might be a dimeric form of gp36 (confirmed by the results shown in FIGS. 8 and 9). The detection of gp80 was not restricted to infected CEM cells, since it was also detectable in HIV-2 infected T4 lymphocytes (data not shown).

Comparison of the results obtained by Western blot analysis and the immunoprecipitation assays showed that patient sera, anti-gp300 polyclonal antibodies, and mAb 1H8 recognize the denatured forms of gp80 and gp125 better than their native forms (FIGS. 1, 2, 3, 4 and 6). Native forms of these mature glycoproteins probably have conformations which mask the epitopes identified by the different antibodies.

VI. Incorporation of Glucosamine and Fucose in gp80

Extracts from HIV-2 infected cells metabolically labeled with [$^3$H] glucosamine and [$^3$H] fucose were immunoprecipitated using mAb 1H8 and anti-gp300 polyclonal antibodies. In accord with the previous results (FIGS. 3–6), anti-gp300 antibodies immunoprecipitated sugar labeled gp300, gp140, gp125, and gp80, whereas mAb 1H8 immunoprecipitated gp300, gp140, and gp80. All these proteins incorporated [$^3$H] glucosamine, whereas incorporation of [$^3$H] fucose mainly occurred in gp125 and gp80 (FIG. 7a). In these experiments, the labeling of gp36 with [$^3$H] glucosamine was observed faintly after a prolonged exposure of the autoradiogram (data not shown; similar to FIG. 1, Rey et al., 1989). The glycoprotein gp80 also can incorporate [$^3$H] mannose as is the case for gp300, gp140, and gp125 (data not shown). Incorporation of these labeled sugars in gp80 and in other glycoproteins was completely blocked by tunicamycin, an antibiotic which inhibits N-linked glycosylation of proteins (data not shown).

Asparagine-linked oligosaccharides (containing N-acetylglucosamine, mannose, and glucose) of glycoproteins undergo extensive processing after their attachment to nascent proteins (Kornfeld and Kornfeld, 1985). Oligosaccharide chains become trimmed in the endoplasmic reticulum and in the Golgi apparatus before the transfer of fucose and sialic acid residues. Therefore, incorporation of fucose residues occurs late in the glycosylation pathway. Accordingly, in HIV-2 infected cells [$^3$H] fucose becomes incorporated mainly in gp125 and gp80, two proteins which are mature products of the HIV-2 envelope precursor (see FIGS. 6 and 7).

To confirm that gp80 was produced during the processing of envelope precursor, HIV-2 infected cells were labeled with [$^{35}$S] methionine in the absence or presence of the glucosidase inhibitor, castanospermine (Saul et al., 1983). Culture supernatants were then assayed by immunoprecipitation using an HIV-2 positive patient serum which recognizes several viral proteins. In the presence of castanospermine, production of gp80 and gp125 were markedly reduced, whereas the production of the major core protein (p26) was not significantly affected (FIG. 7b).

VII. Dissociation of gp80 into gp36

Preliminary experiments suggested that gp80 could be dissociated to give gp36. For this reason, experiments were carried out to optimize conditions under which the dissociation of gp80 might occur, such as, high salt, acidic pH, ionic detergent, EDTA, and EGTA.

Previously, it was reported that the dimeric form of the envelope precursor (gp300) can be dissociated by incubation in slightly acidic buffer (Rey et al., 1989). Although this latter method also works for gp80, but in a buffer less than pH 6, most of gp80 becomes degraded. In all experiments, extracts were prepared from infected cells or from viral pellets by a lysis buffer containing non-ionic detergent, Triton X-100. Under these conditions, gp30 and gp80 are not dissociated even after addition of the ionic-detergent SDS.

The effect of SDS was investigated when it is used instead of Triton for the preparation of extracts. HIV-infected cells were labeled with [$^{35}$S] methionine before preparation of extracts by solubilization in lysis buffer containing either 1% Triton X-100 or 1% SDS. These extracts were then diluted 10 fold in lysis buffer without detergent and immunoprecipitated using mAb 1H8. The immune-compiex preparations from Triton-extracts showed the presence of [$^{35}$S] methionine-labeled bands corresponding to gp300, gp140, gp80 and a faint-band of gp36 (FIG. 8, section C lane 1). On the other hand, when extracts were prepared with SDS, then gp300 and gp80 were almost undetectable whereas the level of gp140 and gp36 was increased (FIG. 8, section C lane 2). Thus in the presence of ionic detergent, the dimeric forms gp300 and gp80 were dissociated giving rise to gp140 and gp36, respectively. Dissociation of the purified [$^{35}$S] methionine labeled gp300 gives only gp140 (Rey et al., 1989). Accordingly, gp36 should arise from the dissociation of gp80.

It should be noted that the degradation of proteins occurred also in the presence of SDS since not all the label in gp300 and gp80 was recovered in the dissociated proteins (FIG. 8, section C). The presence of 200 units/ml aprotinin and 0.2 mM PMSF did not prevent such degradation during incubation with SDS. It might be that the dimeric forms of proteins have a conformation which can resist proteolysis. Dissociation of gp300 and gp80 might then lead to conformational modifications making the proteolytic sites accessible.

Dissociation experiments were also carried out with the HIV-2 pellet. [$^{35}$S] methionine labeled viral proteins were solubilized in lysis buffer containing 1% Triton or 1% SDS and in RIPA buffer containing 0.1% SDS and 1% deoxycholate. Extracts in 1% SDS lysis buffer were also heated at 95° C. All the extracts were then immunoprecipitated with mAb 1H8 and analyzed by polyacrylamide gel electrophoresis (FIG. 8, section V). In the immune-complex prepared from Triton-extracts, gp80 and gp36 were the major proteins immunoprecipitated by mAb 1H8. On the other hand, gp80 became undetectable whereas the level of gp36 was slightly increased in SDS-extracts. The degree of degradation in SDS-extracts must have been dramatic since most of the label disappeared. A somewhat better result was observed with the RIPA buffer in which most of gp80 was dissociated and about 30% of the label was recovered in gp36 (FIG. 8, section V, lane 4).

In order to show that gp80 is composed of only gp36, dissociation experiments were carried out using [$^{35}$S] methionine labeled gp80 purified by mAb 1H8 immunoprecipitation and by preparative gel electrophoresis. Lyophilized gp80 preparations were then suspended directly in an acetate buffer with SDS at pH 6.8, 5.8, and 4.8. At pH 4.8, all gp80 was converted to gp36 (FIG. 9).

VIII. The Transmembrane Glycoprotein of SIV-mac Exists in a Dimeric Form

Previously, it was shown that the glycoprotein precursor (gp140) of SIV forms a dimer during its processing (Rey et al., 1989). For this reason it was important to investigate whether the transmembrane glycoprotein was also detectable as a dimer. SIV and HIV-2 infected cells were labeled with [$^3$H] glucosamine and extracts prepared by lysis buffer containing Triton were immunoprecipitated with mAb 1H8. As in FIG. 7, the monoclonal antibody precipitated gp300, gp140, and gp80 from HIV-2 infected cells. In addition, a very faint band corresponding to gp36 was detected (FIG. 10). In SIV infected cells, the monoclonal antibody precipitated three glycosylated proteins: the envelope precursor gp140, the dimer precursor gp300, and a 65 kDa protein (gp65) which was probably the counterpart of HIV-2 gp80 (FIG. 10). As gp80, gp65 was found to be associated with SIV virus particles.

It should be noted that in these experiments, monomeric forms of the transmembrane glycoprotein of HIV-2 ROD and SIV-mac were not detectable. The HIV-2 ROD amino-acid sequence 579–604 corresponds to SIV-mac sequence 595–620 (5,16). Since these two sequences are highly homologous, then mAb 1H8 cross-reacts with envelope proteins of both HIV-2 ROD and SIV-mac.

By the use of a monoclonal antibody, Veronese et al. (33) have recently reported that the transmembrane glycoprotein of SIV-mac is a 32 kDA protein (gp32). However, in their immunoprecipitation assays, they reported the presence of unidentified 75 and 300 kDa proteins at high levels along with the envelope precursor gp140. In analogy with the data herein, the 75 kDa protein is probably the dimeric form of the transmembrane glycoprotein gp32 (FIG. 10), whereas the 300 kDa protein should be the dimeric form of the envelope precursor previously reported (29).

This invention thus elucidates the processing of HIV-2 envelope glycoprotein. The unusual feature of this processing is that the envelope precursor requires the formation of a homologous dimer in order to become transported and processed through the Golgi apparatus (Rey et al., 1989). The precursor gp140 becomes dimerized in the rough endoplasmic reticulum and the resulting gp300 dimer intermediary precursor is then transported to the Golgi apparatus where it is further processed. Finally, the dimer is transported to the plasma membrane and cleaved by the cellular protease to yield the mature HIV-2 envelope glycoproteins: the extracellular glycoproteins (gp125) in monomeric forms and the transmembrane glycoproteins (gp36) in dimeric forms (gp80) (FIG. 11).

Referring to FIG. 11, the envelope polypeptide during its synthesis becomes glycosylated to give rise to the "hypothetical glycoprotein precursor" gp150 which becomes rapidly trimmed by the rough endoplasmic reticulum (RER) glucosidases I and II and mannosidase to give rise to gp140. This monomer becomes dimerized and the resulting gp300 "dimer intermediary precursor" is then transported to the Golgi apparatus. Further trimming of gp300 is carried out by the Golgi mannosidases before transfer of fucose and sialic acid residues in the medial and trans Golgi. Finally, the dimer is cleaved by the cellular protease to yield the extracellular envelope glycoprotein (ECG) gp125 and the dimeric form of the transmembrane glycoprotein (TMG), gp80.

In a previous study (Rey et al., 1989), it was suggested that the processed gp300 becomes dissociated before transport to the plasma membrane. This is probably not the case, because now there is evidence to indicate that the transmembrane proteins become produced as homodimers. In the previous study, monensin was used as an inhibitor of the transport of membrane glycoproteins and secretory proteins from the Golgi apparatus (Johnson and Schlesinger, 1980). In the presence of monensin, a 135-KDa protein (gp135), which might have been the dissociated product of gp300, was accumulated in HIV-2 infected cells. This production of gp135 was probably an artifact triggered by monensin due to accumulation of the processed gp300 in the Golgi apparatus.

The mechanism of dimerization of the envelope glycoprotein precursor is not yet clear. This is an intrinsic property of the polypeptide moiety of the envelope precursor. The fact that the transmembrane glycoproteins exist in dimeric forms (gp80), suggests that dimerization of gp140 occurs through interactions between the transmembrane regions of the envelope precursor. Dissociation of the dimeric forms (gp300 and gp80) might occur at slightly acidic pH. Accordingly, dimerization of gp140 might be pH dependent and occurs in a compartment in the rough endoplasmic reticulum which favors the fusion of two gp140 precursor molecules.

Several observations indicate that formation of gp300 is not an artifact observed in HIV-2 infected CEM cells: (1) Pulse-chase experiments in HIV-2 infected CEM cells indicate that gp140 is first synthesized before the formation of gp300 which is itself detected few hours before the production of mature envelope proteins, gp125 and gp80; (2) A similar kinetics for the detection of gp140, gp300, gp125, and gp80 is also observed in T4 lymphocytes infected with HIV-2; (3) The fate of gp140 is the formation of gp300. This latter is well illustrated by experiments in which transport of the dimer from the endoplasmic reticulum to the Golgi apparatus is blocked by glucosidase inhibitors. In the presence of these inhibitors, all monomer precursors synthesized by pulse-labeling of infected cells become dimerized during the period of chase. Dimerization of gp140 is also not a consequence of experimental conditions in our studies. Pulse-chase experiments carried out at reduced temperatures (15–20° C.) to block transport in the endoplasmic reticulum, show that the monomer precursors synthesized by pulse-labeling of infected cells do not form dimers when the chase is carried out at reduced temperatures. Thus, these results indicate that formation of gp300 requires transport of gp140 in a compartment with an environment favoring the process of dimerization. All these observations (Rey et al., 1989) emphasize that dimerization is a natural step in the processing pathway of gp140, i.e., dimerization is not due to accumulation of unprocessed gp140, nor is it an artifact of the experimental procedure.

The molecular weight of the dimeric form of the envelope precursor had been estimated by polyacrylamide gel electrophoresis under denaturing conditions (Rey et al., 1989). In a 5% polyacrylamide gel containing 0.1% bisacrylamide instead of 0.2% (wt/vol), this dimeric precursor migrated at a position corresponding to a 280-kDa protein (data not shown). In order to confirm the molecular weight of this dimer under native conditions, gel filtration experiments were carried out using an S-300 Sephacryl column and [$^{35}$S] methionine labeled extracts from HIV-2 infected cells prepared by lysis buffer containing Triton. Under these experimental conditions, gp300 eluted as the second peak after the peak of aggregated proteins. The transmembrane glycoprotein dimer eluted as a 75–80 kDA protein after the peak of gp125 and before the peak of bovine-serum-albumin (68 kDa) marker (data not shown). These observations indicate that the molecular weight estimations of the native and denatured dimers gp300 and gp80 are comparable. In vitro, the dissociation of these dimeric forms occurred in acidic pH and also in the presence of the ionic-detergent SDS. When extracts were prepared in the lysis buffer containing Triton, then the dimeric forms gp300 and gp80 resisted dissociation by SDS. The non-ionic detergent Triton, therefore, conserved the native forms of the envelope dimers, gp300 and gp80.

Dimeric forms of the envelope precursor and the transmembrane glycoprotein were also observed in cells infected with SIV but not with HIV-1. In the case of HIV-1, it has been reported that a small proportion of the transmembrane glycoprotein in the HIV-1 particles might exist as a dimer linked by disulfide bonds (Bharat Parekh and Roger Walker, personal communication). The transmembrane dimers of HIV-2 (gp80) and SIV (gp65), however, resist dissociation by reducing agents. Accordingly, dimerization of the envelope glycoprotein precursor can be considered a specific property of HIV-2 and SIV envelope gene expression. This property could be used for characterization of new HIV isolates, as a convenient marker to describe their relationship to HIV-1 or HIV-2. Dimerization of the envelope precursor might be required for the processing of the envelope precursor to yield the mature envelope glycoproteins. The dimeric form of the transmembrane glycoprotein might be essential for optimal structure of the virion and thus its capacity to fuse with the cellular membrane and be infectious. In vitro dissociation of the transmembrane dimer leads to a dramatic degradation. It might be, therefore, that the dimeric forms of this glycoprotein have a conformation which resists proteolysis.

Previously, the formation of oligomeric complexes of some viral structural glycoproteins has been reported. For example, the hemagglutinin (HA) of influenza virus exists as a trimer which could be stabilized by cross-linking agents (5, 36, 37). The G glycoprotein of the vesicular stomatitis virus (VSV) also forms a trimer (11, 24). More recently, the envelope glycoprotein precursor of the Rous sarcoma virus was reported to form a trimer held by a disulfide linkage (12). In all these studies, formation of oligomeric complexes has been associated with their intracellular transport from the endoplasmic reticulum. In the case of the RSV the trimeric structure of the transmembrane glycoprotein seems to be the functional form found in virions. Therefore, the results observed in the RSV are analogous with those presented here, i.e., oligomerization of the HIV-2 and SIV envelope glycoprotein precursor and the transmembrane glycoprotein. In contrast to the RSV however, the dimeric forms of the HIV-2 and SIV are stable and are not dissociated by reducing agents. Nevertheless, all these observations enforce the suggestion that efficient processing of some glycoproteins requires tne formation of oligomeric structures, and in some cases oligomeric forms of the mature glycoprotein might be essential for infectivity. Accordingly, antiviral agents designed to block the formation of oligomeric precursors or cause dissociation of oligomeric complexes of the mature proteins, might be employed to prevent virus replication and its spreading.

Following is a more detailed description of the experimental procedures used in this invention.

Materials

L-[$^{35}$S] Methionine (specific activity >1000 $\mu$Ci/mmol, L-[6-$^3$H] Fucose (specific activity: 45–70 $\mu$Ci/mmol), D-[6-$^3$H] Glucosamine (specific activity: 20–40 $\mu$Ci/mmol) were purchased from Amersham (Amersham, UK). Castanospermine and tunicamycin were obtained from Boehringer-Mannheim (Manneheim, West Germany). Poly(A)·poly(U) was the generous gift of M. Michelson, Institut Curie, Paris, and is prepared according to Hovanessian et al. (J. Interferon Res. 1982, 2:209–216).

Virus and Cells

HIV-1$_{BRU}$ isolate of the human immunodeficiency virus type 1 (Montagnier et al., 1984), HIV-2$_{ROD}$ isolate of the human immunodeficiency virus type 2 (Clavel et al., 1986), and Simian immunodeficiency virus, SIVmac$_{142}$ (Daniel et al., 1985) were used in this study.

The different cell lines and human lymphocytes were cultured in suspension medium RPMI-1640 (GIBCO-BRL, Cergy-Pontoise France) containing 10% (v/v) fetal calf serum; 2 $\mu$g/ml Polybrene (Sigma) was added for HIV infected cell cultures. CEM clone 13 cells are derived from the human lymphoid cell line CEM (ATCC-CCL119) and express the T4 antigen to a high level. Five days after infection with HIV-1$_{BRU}$ or HIV-2$_{ROD}$ isolates, about 80–90% of the cells produce viral particles and can be identified by a cytopathic effect corresponding to vacuolisation of cells and appearance of small syncitia. The HUT-78 cell line is another human T4 positive lymphoid cell line (Gazdar et al., 1980) that is highly permissive for the replication of SIVmac$_{142}$ (Daniel et al., 1985). Peripheral blood lymphocytes from healthy blood donors were stimulated for three days with 0.2% (w/v) phytohemagglutinin fraction P (Difco, Detroit, USA) in RPMI-1640 medium supplemented with 10% fetal calf serum. Cells were then cultured in RPMI-1640 medium containing 10% (v/v) T cell growth factor (TCGF, Biotest). After infection with HIV-2. lymphocytes were cultured in presence of 10% (v/v) TCGF and 2 $\mu$g/ml Polybrene.

Metabolic Labeling of Cells

For metabolic labeling of proteins, infected cells were incubated for 16 hours at 37° C. in MEM culture without L-methionine and serum, but supplemented with 200 $\mu$Ci/ml [$^{35}$S] methionine. For metabolic labeling of glycoproteins, infected cells were in cubated for 16 hours at 37° C. in MEM culture medium lacking serum and glucose but supplemented with 200 $\mu$Ci/ml $^3$H-Fucose or 200 $\mu$Ci/ml $^3$H-glucosamine.

Cells and Viral Extracts

Cell pellets corresponding to 10$^7$ cells were resuspended in 100 $\mu$l of buffer: 10 mM Tris-HCl pH 7.6, 150 mM NaCl, 1 mM EDTA, 0.2 mM PMSF, 100 units/ml aprotinin (Iniprol, Choay) before addition of 100 $\mu$l of the same buffer containing 2% (v/v) Triton X-100. Cell extracts were centrifuged at 12,000 g for 10 minutes, and the supernatant was stored at −80° C. until used. For viral extract preparations, 100 μl of 10X lysis buffer (100 mM Tris-HCl pH 7.6, 1.5M NaCl, 10 mM EDTA, 10% (v/v) Triton X-100, 100 units/ml aprotinin) were added per ml of clarified supernatant from infected CEM cells and processed as above. For the preparation of extracts from virus pellets, culture medium from infected cells was first centrifuged at 12,000 g for 10 minutes before high speed centrifugation at 100,000 g for 30 to 60 min. Virus pellets (material from $10^7$ cells) were then solubilized in 200 μl of lysis buffer.

Preparation of an Immunoadsorbant with Antibodies from an HIV-2 Seropositive Patient Immunoglobulins from the serum of an HIV-2 seropositive patient were precipitated with 50% $(NH_4)_2SO_4$, dissolved in 20 mM sodium phosphate (pH 8.0) and further purified on a DEAE cellulose column (DE52, Whatman) by elution with 20 mM sodiam phosphate (pH 8.0). Immunogiobulins purified in this manner were judged to be 90% pure. The antibodies were subsequently coupled to CNBr-activated Sepharose CL 4B according to a technique described (Berg, 1977). Two milligrams of IgG were coupled per ml of Sepharose CL 4B. This immunoadsorbant is referred to as HIV-2 serum-Sepharose.

Preparation of HIV-2 Proteins on an Immunoaffinity Column

Cell extracts from HIV-2 producing CEM cells were first diluted in two volumes of binding buffer (20 mM Tris-HCl pH 7.6, 50 mM KCl, 150 mM NaCl, 1 mM EDTA, 1% (v/v) glycerol, 7 mM β-mercaptoethanol, 0.2 mM PMSF, 100 units/ml aprotinin) before incubation with one volume of HIV-2 serum-Sepharose. Supernatants from HIV-2 producing cells were processed as cell extracts except that only one tenth of binding buffer concentrate 10X was added per volume of supernatant. The binding was carried out overnight, then the column was washed batchwise in binding buffer. Proteins bound to the column were eluted by boiling in electrophoresis sample buffer (125 mM Tris-HCl pH 6.8, 1% (w/v) SDS, 2M urea, 20% glycerol, 0.5% β-mercaptoethanol). Eluted proteins were resolved by electrophoresis on 7.5% polyacrylamide-SDS gels containing 6M urea and 0.1% bisacrylamide instead of 0.2% (w/v).

Preparative Electrophoresis

HIV-2 glycoproteins (gp300 or gp80) eluted from the affinity column were resolved by polyacrylamide gel electrophoresis as previously described, and the regions of the gel containing the viral glycoproteins were cut out by reference to the position of prestained molecular weight protein markers (BRL). Glycoprotein gp300 was eluted by incubation for 16 hours at 4° C. in elution buffer (0.1M $NaHCO_3$, 0.5 mM EDTA, 0.05% (w/v) SDS, 0.2 mM PMSF). The glycoprotein fractions thus obtained were lyophilized and kept refrigerated until used. Glycoprotein gp80 was electroeluted in buffer containing 4 mM Tris-HCl pH 7.6, 2 mM sodium acetate, and 2 mM EDTA.

Preparation of Murine Polyclonal Antibodies, Anti-gp300

HIV-2 envelope glycoprotein gp300 was purified from extracts of infected CEM cells ($3\times10^8$ cells) by immunoaffinity chromatography on the HIV-2 serum-Sepharose and followed by preparative gel electrophoresis (Rey et al., 1989). The purified preparation of gp300 was dissolved in 10 ml of 150 mM NaCl containing 0.5M urea and 1 mg/ml of mouse serum proteins and dialyzed for 24 hours against the solution containing 150 mM NaCl and 0.5M urea. The dialysate was then centrifuged and 2 ml aliquots were stored at −80° C.

Five mice (8 weeks old) were injected intraperitoneally, five times at 12 days interval with 350 μl of the gp300 preparation (about 0.1 μg of gp300). Poly(A)·poly(U) (200 μg; 1 mg/ml in 150 mM NaCl) was used as an adjuvant which was administered intravenously during each immunization (Hovanessian et al., 1988). Five days before the last injection, mice were injected intraperitoneally with a suspension of $10^6$ sarcoma 180/TG cells to prepare hyperimmune ascitic fluid (Hovanessian et al., 1988). A week following the booster, mice were sacrificed and the ascitic fluids were collected. Ascitic cells were removed by centrifugation (200 g, 5 min) and the peritoneal fluid was collected.

Production and Characterization of Monoclonal, mAb 1H8

HIV-2 ROD virions were cultivated in CEM cells and purified from concentrated culture supernatants by banding in sucrose gradients. Purified virus was disrupted in 0.5% Triton X-100, 150 nM NaCl, 50 mM Tris, pH 8.0, 1% aprotinin (Sigma) and clarified by ultra-centrifugation. The viral extract was then passed over a Lentil-Lectin Sepharose 4B affinity column (Pharmacia), the column washed, and the bound glycoproteins eluted with 0.5 M methyl a-D-monnopyranoside (Sigma), and dialyzed overnight against phosphate-buffered saline. BALB-C mice were immunized intraperitoneally with 0.3 mls of purified glycoproteins (2–5 μg) reattached to Lentil-Lectin Sepharose 4B (50–100 μl). The mice were boosted every 4–6 weeks for 24 weeks with the same immunogen and monitored for HIV-2 glycoprotein antibodies qualitatively by RIPA of [$^{35}$S] methionine labeled HIV-2 virion extracts and quantitatively on the Genetic Systems HIV-2 disrupted virion EIA. Three days after the last injection, spleen cells were fused with NSI myeloma cells according to the method of Kohler and Milstein (22). 96-well fusion plates were screened by hybridomas secreting anti-HIV-2 antibodies using the Genetic Systems HIV-2 disrupted virion EIA. Methods for the propagation and stabilization of cloned hybridomas and for ascites production have been previously described (16). Hybridoma culture supernatants were screened by RIPA and Western blot analysis. Monoclonal antibody (mAb) 1H8, which reacted with the transmembrane glycoprotein, was further mapped to amino-acid squence 579–604 within the HIV-2 transmembrane glycoprotein using a synthetic peptide based EIA (32). The HIV-2 amino-acid sequence 579–604 is highly conserved among all HIV-2 and SIV isolates thus far sequenced accordingly, monoclonal antibody 1H8 cross-reacts with HIV-2 and SIV isolates thus far tested. The synthetic peptide p39' was synthesized according to the amino-acid sequence 579–604 deduced from the nucieotide sequence of the HIV-2 ROD envelope. The amino-acid sequence of peptide p39' is the following

VTAIEKYLQDQARLNSWGCAFRQVCH.

Radio-immunoprecipitation Assay (RIPA)

Cell or viral extracts (20 μl) (material corresponding to $1\times10^6$ infected cells) were first diluted in two volumes of RIPA buffer [(10 mM Tris-HCl pH 7.6, 150 mM NaCl, 1 mM EDTA, 1% Triton X-100 (v/v), 0.2% sodium deoxycholate (wt/v), 0.1% SDS (wt/v), 7 mM 2 β-mercaptoethanol, 0.2 mM PMSF, 100 units/ml of aprotinin (Iniprol, Choay)]. Diluted extracts were then incubated (45 min, 4° C.) with polyclonal or monoclonal antibodies (2–5 μl). Protein A-Sepharose was then added and the samples were further incubated for 3 hr at 4° C. These samples were washed in the RIPA buffer. Proteins recovered by immunoprecipitation were eluted by heating (95° C., 5 min) in the electrophoresis sample buffer [125 mM Tris- HCl, pH 6.8, 1% SDS (wt/v), 20% glycerol (v/v), 1% 2 β-mercaptoethanol]. Eluted proteins were resolved by electrophoresis in 7.5–12.5% polyacrylamide SDS gels containing 0.1% bisacrylamide instead of 0.2% (wt/v).

Electrophoretic Transfer Immunoblot Analysis: Western Blot

Proteins were subjected to analysis by polyacrylamide gel electrophoresis before being electrophoretically transferred to 0.45 μm nitrocellulose sheets (Schleicher and Schull, Dassel, FRG) in electrode buffer (20 mM Tris base, 150 mM glycine, 20% methanol, v/v) as described (Burnette 1981). The electrophoretic blots were saturated with 5% (w/v) non-fat dry milk in PBS (Johnson et al., 1984). They were then incubated in a sealed bag (overnight 4° C.) either with HIV-1 or HIV-2 positive sera (at 1:100 dilution) or with mouse polyclonal or monoclonal antibodies (at 1:200 dilution) in PBS containing 10% FCS. The sheets were subsequently washed in PBS, PBS containing 5% Nonidet P-40 and then resaturated in PBS containing non-fat milk (5%). The washed sheets were then incubated (2 hr, room temperature) in a sealed bag either with a preparation of $^{125}$I-labeled protein A (Amersham, >30 mCi/mg) to reveal the human polyclonal antibodies in the HIV-1 or HIV-2 sera or with a preparation of $^{125}$I-labeled goat anti-mouse immunoglobulins (Amersham; 2–10 μCi/μg). The sheets were removed from the bags and washed again, dried and autoradiographed (Kodak RP Royal, X-Ray films) for 24–48 hr.

It will be understood that the present invention is intended to encompass the Previously described proteins and glycoproteins in purified form, whether or not fully glycosylated, and whether obtained using the techniques described herein or other nethods. In a preferred embodiment of this invention, the retrovirus and polypeptides are substantially free of human tissue and human tissue components, nucleic acids, extraneous proteins and lipids, and adventitious microorganisms, such as bacteria and viruses. It will also be understood that the invention encompasses equivalent proteins and glycoproteins having substantially the same biological and immunogenic properties. Thus, this invention is intended to cover serotypic variants of the proteins and glycoproteins of the invention.

The proteins and glycoproteins of this invention can be obtained by culturing HIV-2 in susceptible mammalian cells of lymphocytic lineage, such as T-lymphocytes or pre-T-lymphocytes of human origin or non-human primate origin (e.g. chimpanzee, African green monkey, or macaques.) A number of different lymphocytes expressing the CD4 phenotypic marker can be employed. Examples of suitable target cells for HIV-2 infection are mononuclear cells prepared from peripheral blood, bone marrow, and other tissues from patients and donors. Alternatively, established cell lines can be employed. For example, HIV-2 can be propagated on blood-donor lymphocyte cultures, followed by propagation on continuous cell strains of leukemic origin, such as HUT 78. HUT 78 is a well characterized mature human T cell line, which has been deposited at Collection Nationale Des Cultures De Micro-organismes (CNCM) at the Pasteur Institut in Paris, France on Feb. 6, 1986, under culture collection deposit accession number CNCM I-519. Another suitable target for HIV-2 infection and production of the proteins and glycoproteins of the invention is the T-cell line derived from an adult with lymphoid leukemia and termed HT. HT cells continuously produce virus after parental cells are repeatedly exposed to concentrated cell culture fluids harvested from short-term culture T-cells grown in TCGF that originated from patients with LAS or AIDS. In addition, there are several other T or pre-T human cell lines. such as CEM and MOLT 3 that can be infected and continue to produce HIV-2. Furthermore, B-lymphoblastic cell lines can also be productively infected by HIV. Montagnier et al, Science, 225:63–66(1984).

The proteins and glycoproteins of the invention can be produced in the target cells using the culture conditions previously described, as well as other standard techniques. For instance, infected human lymphocytes can be stimulated for three days by phytohemaglutinin (PHA). The lymphocytes can be cultured in RPMI-1640 medium to which has been added 10% fetal calf serum, $10^{-5}$M beta mercaptoethanol, interleukin 2, and human alpha anti-interferon serum. Barre-Sinoussi et al, Science, 220:868–871 (1983). In addition, techniques for the-propagation of HIV-2 in HUT 78 and CEM cell lines are described in copending U.S. application Ser. No. 835,228, filed Mar. 3, 1986, the entire disclosure of which is relied upon and incorporated by reference herein.

The production of virus in the cell cultures can be monitored using several different techniques. Supernatant fluids in the cell cultures can be monitored for viral reverse transcriptase activity. Electron microscopic observation of fixed and sectioned cells can also be used to detect virus. In addition, virus can be detected by transmitting the virus to fresh normal human T-lymphocytes (e.g., umbilical cord blood, adult peripheral blood, or bone marrow leukocytes) or to established T-cell lines. Testing for antigen expression by indirect immunofluorescence or Western Blot procedures using serum from seropositive donors can also be employed. In addition, nucleic acid probes can be utilized to detect viral production.

After a sufficient period of time for viral multiplication to take place, infected cells can be separated from the culture medium and disrupted to expose intracellular proteins using conventional techniques. For example, physical shearing, homogenization, sonication, detergent solubilization, or freeze-thawing can be employed. The viral proteins released by these cells can be separated from the other cellular components and purified using standard biochemical procedures. For example, virus can be recovered by ultra centrifugation, and the viral proteins can then be solubilized by detergent and then purified by gel filtration, ion-exchange chromatography, affinity chromatography, dialysis, or by the use of monoclonal antibodies or by combinations of these procedures. A thorough purification of the antigens of the invention can be performed by immunoreaction with the sera of patients known to possess antibodies effective against the antigens, with concentrated antibody preparations such as polyclonal antibodies, or with monoclonal antibodies directed against the antigens of the invention.

The proteins and the glycoproteins of the present invention can be used as antigens to identify antibodies to HIV-2 and SIV in materials and to determine the concentration of the antibodies in those materials. Thus, the antigens can be used for qualitative or quantitative determination of the retrovirus in a material. Such materials of course include human tissue and human cells, as well as biological fluids, such as human body fluids, including human sera. When used as a reagent in an immunoassay for determining the presence or concentration of the antibodies to HIV-2, the antigens of the present invention provide an assay that is convenient, rapid, sensitive, and specific.

More particularly, the antigens of the invention can be employed for the detection of HIV-2 by means of immunoassays that are well known for use in detecting or quantifying humoral components in fluids. Thus, antigen-antibody interactions can be directly observed or determined by secondary reactions, such as precipitation or agglutination. In addition, immunoelectrophoresis techniques can also be employed. For example, the classic combination of electrophoresis in agar followed by reaction with anti-serum can be utilized, as well as two-dimensional electrophoresis, rocket electrophoresis, and immunelabeling of polyacrylamide gel patterns (Western Blot or immunoblot.) Other immunoassays in which the antigens of the present invention can be employed include, but are not limited to, radioimmunoassay, competitive immunoprecipitation assay, enzyme immunoassay, and immunofluorescence assay. It will be understood that turbidimetric, calorimetric, and nephelometric techniques can be employed. An immunoassay based on Western Blot technique is preferred.

Immunoassays can be carried out by immobilizing one of the immunoreagents, either an antigen of the invention or an antibody of the invention to the antigen, on a carrier surface while retaining immunoreactivity of the reagent. The reciprocal immunoreagent can be unlabeled or labeled in such a manner that immunoreactivity is also retained. These techniques are especially suitable for use in enzyme immunoassays, such as enzyme linked immunosorbent assay (ELISA) and competitive inhibition enzyme immunoassay (CIEIA).

When either the antigen of the invention or antibody to the antigen is attached to a solid support, the support is usually a glass or plastic material. Plastic materials molded in the form of plates, tubes, beads, or disks are preferred. Examples of suitable plastic materials are polystyrene and polyvinyl chloride. If the immunoreaqent does not readily bind to the solid support, a carrier material can be interposed between the reagent and the support. Examples of suitable carrier materials are proteins, such as bovine serum albumin, or chemical reagents, such as gluteraldehyde or urea. Coating of the solid phase can be carried out using conventional techniques.

Depending on the use to be made of the proteins and glycoproteins of the invention, it may be desirable to label them. Examples of suitable labels are radioactive labels, enzymatic labels, fluorescent labels, chemiluminescent labels, and chromophores. The methods for labeling proteins and glycoproteins of the invention do not differ in essence from those widely used for labeling immunoglobulin. The need to label nay be avoided by using labeled antibody to the antigen of the invention or anti-immunoglobulin to the antibodies to tne antigen as an indirect marker.

Once the proteins and glycoproteins of the invention have been obtained, they can be used to produce polyclonal and monoclonal antibodies reactive therewith. Thus, a protein or glycoprotein of the invention can be used to immunize an animal host by techniques known in the art. Such techniques usually involve inoculation, but they may involve other modes of administration. A sufficient amount of the protein or the glycoprotein is administered to create an immunogenic response in the animal host. Any host that produces antibodies to the antigen of the invention can be used. Once the animal has been immunized and sufficient time has passed for it to begin producing antibodies to the antigen, polyclonal antibodies can be recovered. The general method comprises removing blood from the animal and separating the serum from the blood. The serum, which contains antibodies to the antigen, can be used as an antiserum to the antigen. Alternatively, the antibodies can be recovered from the serum. Affinity purification is a preferred technique for recovering purified polyclonal antibodies to the antigen, from the serum.

Monoclonal antibodies to the antigens of the invention can also be prepared. One method for producing monoclonal antibodies reactive with the antigens comprises the steps of immunizing a host with the antigen; recovering antibody-producing cells from the spleen of the host; fusing the antibody-producing cells with myeloma cells deficient in the enzyme hypoxanthine-guanine phosphoribosyl transferase to form hybridomas; selecting at least one of the hybridomas by growth in a medium comprising hypoxanthine, aminopterin, and thymidine; identifying at least one of the hybridomas that produces an antibody to the antigen; culturing the identified hybridoma to produce antibody in a recoverable quantity; and recovering the antibodies produced by the cultured hybridoma.

These polyclonal or monoclonal antibodies can be used in a variety of applications. Among these is the neutralization of corresponding proteins. They can also be used to detect viral antigens in biological preparations or in purifying corresponding proteins, glycoproteins, or mixtures thereof, for example when used in affinity chromatographic columns.

The invention provides immunogenic proteins and glycoproteins, and more particularly, protective polypeptides for use in the preparation of vaccine compositions against HIV-2. These polypeptides can thus be employed as viral vaccines by administering the polypeptides to a mammal susceptible to HIV-2 infection. Conventional modes of administration can be employed. For example, administration can be carried out by oral, respiratory, or parenteral routes. Intradermal, subcutaneous, and intramuscular routes of administration are preferred when the vaccine is administered parenterally.

The ability of the proteins, glycoproteins, and vaccines of the invention to induce protective levels of neutralizing antibody in a host can be enhanced by emulsification with an adjuvant, ncorporation in a liposome, coupling to a suitable carrier, or by combinations of these techniques. For example, the proteins and glycoproteins of the invention can be administered with a conventional adjuvant, such as aluminum phosphate and aluminum hydroxide gel, in an amount sufficient to potentiate humoral or cell-mediated immune response in the host. Similarly, the polypeptides can be bound to lipid membranes or incorporated in lipid membranes to form liposomes. The use of nonpyrogenic lipids free of nucleic acids and other extraneous matter can be employed for this purpose.

The immunization schedule will depend upon several factors, such as the susceptibility of the host to infection and the age of the host. A single dose of the vaccine of the invention can be administered to the host or a primary course of immunization can be followed in which several doses at intervals of time are administered. Subsequent doses used as boosters can be administered as needed following the primary course.

The proteins and vaccines of the invention can be administered to the host in an amount sufficient to prevent or inhibit HIV-2 infection or replication in vivo. In any event, the amount administered should be at least sufficient to protect the host against substantial immunosuppression, even though HIV infection may not be entirely prevented. An immunogenic response can be obtained by administering the proteins or glycoproteins of the invention to the host in an amount of about 10 to about 500 micrograms antigen per kilogram of body weight, preferably about 50 to about 100 micrograms antigen per kilogram of body weight. The proteins and vaccines of the invention can be administered together with a physiologically acceptable carrier. For example, a diluent, such as water or a saline solution, can be employed.

Reference is made herein to proteins of the invention. The proteins of the invention include, for example, polypeptides that are not glycosylated. The proteins can be prepared using conventional techniques. For instance, glycosylation of the proteins in vivo can be blocked by tunicamycin, an antibiotic which inhibits N-linked glycosylation of proteins (Schwartz et al., 1976; Kornfeld and Kornfeld, 1985). Alternatively, glycoproteins of the invention can be deglycosylated by β-N-acetylglucosaminase H (endo H), which cleaves high mannose-type oligosaccharide chains (Tarentino et al., J. Biol. Chem., 249: 818–824, 1974).

In summary, proteins and glycoproteins, which are precursors of HIV-2 and SIV envelope glycoprotein and the dimeric form of the transmembrane glycoprotein, have now been identifed. In addition to providing useful tools for detection of antibodies to the retrovirus in humans and for raising neutralizing antibodies to HIV-2 in vitro and in vivo, this invention adds to the base of knowledge relating to immunodeficiency active proteins and glycoproteins of the AIDS viruses.

REFERENCES

1. Barre-Sinoussi, F. Chermann, J. C., Rey, F., Nugeyre, M. T., Chamaret, S., Gruest, J., Dauguet, C., Axler-Blin, C., Brun Vezinet, F., Rouzioux, C., Rozembaum, W. and Montagnier L., 1983. Isolation of a T-lymphotropic retrovirus from a patient at risk for acquired immune deficiency syndrome (AIDS). Science 220:868–871.
2. Berg, K., 1977. Sequential antibody affinity chromatography of human leucocyte interferon. Scand. J. Immunol. 6:77–86.
3. Brun-Vezinet, F., Rey, M. A., Katlama, C., Girard, P. H., Roulot, D., Yeni, P., Lenoble, L., Clavel, F., Alizon, M., Gadelle, S., Madjar, J. J. and Harzic, M., 1987. Lymphadenopathy associated virus type 2 in AIDS-related complex. Lancet i:128–132.
4. Burnette, W. N. 1981. "Western Blotting": Electrophoretic transfer of oroteins from sodium dodecyl sulfate-polyacrylamide gels to unmodified nitrocellulose and radioiodinated detection with antibody and radioionidated protein A. Anal. Biochem. 112:195–230.
5. Chakrabarti, L., Guyader, M., Alizon, M., Daniel, M. D., Desrosiers, R. C., Tiollais, P. and Sonigo, P. 1987. Sequence of simian immunodeficiency virus from macaque and its relationship to other human and simian retroviruses. Nature 328:543–547.
6. Clavel, F., Guetard, D., Brun-Vezinet, F., Chamaret, S., Rey, M. A., Santos-Ferreira, M. O., Laurent, A. G., Dauguet, C., Katlama, C., Rouzioux, C., Klatzmann, D., Champalimaud, J. L. and Montagnier, L. 1986a. Isolation of a new retrovirus from West African patients with AIDS. Science 233:343–346.
7. Clavel, F., Guyader, M., Guetard, D., Salle, M., Montagnier L., and Alizon, M. 1986b. Molecular cloning and polymorphism of the immune deficiency virus type 2. Nature 324:691–694.
8. Cohen, E. A., Terwilliger, J. G., Sodroski, J. G. and Haseltine W. A. 1988. Identification of a protein encoded by the vpu of HIV-1. Nature (London) 334:532–534.
9. Dalgleish, A. G., Beverley, P. C., Clapham, P. R., Crawford, D. H., Greaves, M. F. and Weiss, R. A. 1984. The CD4 (T4) antigen is an essential component of the receptor for the AIDS retrovirus. Nature 312:763–767.
10. Daniel, M. D., Letvin, N. L., King, N. W., Kannagi, M., Sehgal, P. K., Hunt, R. D., Kanki, P. J., Essex, M. and Desrosiers, R. C. 1985. Isolation of a T-cell tropic HTLV-III-like retrovirus from macaques. Science 228:1201–1204.
11. Doms, R. W., Helenius, A. H., and White, J. M. 1985. Membrane fusion activity of influenza hemagglutinin. J. Biol. Chem. 260:2973–2981.
12. Einfeld, D. and Hunter, E. 1988. Oligomeric structure of a prototype retrovirus glycoprotein. Proc. Natl. Acad. Sci. U.S.A. 85:8688–8692.
13. Fultz, P. N., McClure, H. M., Anderson, D. C., Swenson, R. B. Anand, R. and Srinivasan, A., 1986. Isolation of a T-lymphotropic retrovirus from naturally infected sooty mangabey monkeys (Cercocebusatys). Proc. Natl. Acad. Sci. 83:5286–5290.
14. Gething, M. J., McCammnon, K. and Sambrook, J. 1986. Expression of wild-type and mutant forms of influenza hemagglutinin: the role of folding in intracellular transport. Cell 46:939–950.
15. Gosting, L., McClure, J., Dickenson, E., Watanabe, S., Shriver, K., and Goldstein, L. 1987. Monoclonal antibodies to gp 110 and gp 41 of Human Immunodeficiency Virus. Journal of Clinical Microbiology. 25:845–848.
16. Guyader, M., Emerman, M., Sonigo, P., Clavel, F., Montagnier, L. and Alizon, M. 1987. Genome organization and transactivation of the human immunodeficiency virus type 2. Nature 326:662–669.
17. Hovanessian, A. G., Galabru, J., Riviere, Y. and Montagnier, L. 1988. Efficiency of poly(A)poly(U) as an adjuvant. Immunology Today 9:161–162.
18. Johnson, D. C. and Schlesinger, M. J. 1980. Vesicular stomatitis virus and sindbis virus glycoprotein transport to cell surface is inhibited by ionophores. Virology 103:407–424.
19. Johnson, D. A., Gautsch, J. W., Sportsman, J. R., and Elder, j. H. 1984. Improved technique utilizing non fat dry milk for analysis of proteins and nucleic acids transferred to nitrocellulose. Gene Anal. Techn. 1:3–8.
20. Klatzmann, D., Champagne, E., Chamaret, S., Gruest, J., Guetard, D., Hercend, T., Gluckman, J. C. and Montagnier, L. 1984. T-lymphocyte T4 molecule behaves as the receptor for human retrovirus LAV. Nature 312:767–768.
21. Kohler, G., and Milstein, C. 1975. Continuous cultures of fused cells secreting antibody of predefined specificity. Nature, 256:495–497.
22. Kornfeld, R. and Kornfeld, S. 1985. Assembly of asparagine-linked oligosaccharides. Ann. Rev. Biochem. 54:631–664.
23. Kreis, T. F., and Lodish, H. F. 1986. Oligomerization is essential for transport of vesicular stomatitis viral glycoprotein to the cell surface. Cell 46:929–937.
24. Montagnier, L., Chermann, J. C., Barre-Sinoussi, F., Chamaret, S., Gruest, J., Nugeyre, M. T., Rey, F., Dauguet, C., Axler-Blin, C., Brun-Vezinet, F., Rouzioux, C., Saimot, A. G., Rozembaum, W., Gluckman, J. C., Klatzmann, D., Vilmer, E., Griscelli, C., Gazengel, C. and Brunet, J. B. 1984. A new human T-lymphotropic retrovirus: characterization and possible role in lymphadenopathy and acquired immune deficiency syndrome. In human T cell leukemia/lymphoma viruses, edited by Gallo, R. C., Essex, M. E., Gross, L. Cold Spring Harbor Laboratory, New York 1984, pp 363–379.
25. Montagnier, L., Calvel, F., Krust, B., Chamaret, S., Rey, F., Barre-Sinoussi, F., and Chermann, J. C. 1985. Identification and antigenicity of the major envelope glycoprotein of lymphadenopathy Associated Virus. Virology 144:283–289.
26. Popovic, M., Sarngadharan, M. G., Read, E., and Gallo, R. C. 1984. Detection, isolation and continuous production of cytopathic retrovirus (HTLV-III) from patients with AIDS and pre-AIDS. Science, 224:497–500.
27. Ratner, L., Haseltine, W. A., Patarca, R., Livak, K. J., Starcich, B., Josephs, S. F., Doran, E. R., Rafalski, J. A., Whitehorn, E. A., Baumeister, K., Ivanoff, L., Petteway, S. R., Pearson, J. A., Lantenberg, J. A., Papas, T. S., Ghrayen, J., Chang, N. T., Gallo, R. C. and Wong-Staal, F. 1985. Complete nucleotide sequence of the AIDS virus, HTLV-III. Nature (London) 313:277–284.

28. Rey, M. A., Krust, B., Laurent, A. G., Montagnier, L., and Hovanessian, A. G. 1989. Characterization of human immunodeficiency virus type 2 envelope glycoproteins: dimerization of the glycoprotein precursor during processing. J. Virol. 63:647–658.
29. Saul, R., Chambers, J. P., Molyneux, R. J., and Elhein, A. D. 1983. Castanospermine, a tetrahydroxylated alkaloid that inhibits β-glucosidase and β-glucocerebrosidase. Arch. Biochem. Byophys. 221:593–597.
30. Schwartz, R. T., Rohrschneider, J. M., and Schmidt, M. F. G. 1976. Suppression of glycoprotein formation of Semliki Forest, influenza and avian sarcoma virus by tunicamycin. J. Virol. 19:782–791.
31. Shriver, K., Watson, A., Flesher, A., McClure, J., Wierzbicki, D., Houghton, R., Cosand, W., Goldstein, L., and Tam, M. 1988. Advances in the diagnosis of blood virus infections. In de la Maza LM, Peterson EM (eds.), Medical Virology VII, pp 209–224.
32. Veronese, F. D. M., Joseph, B., Copeland, T. D., Oroszlan, S., Gallo, R. C. and Sargadharan, M. G. 1989. Identification of simian immunodeficiency virus SIV-mac env gene products. J. Virology. 63:1416–1419.
33. Wain-Hobson, S., Sonigo, P., Danos, O., Cole, S., and Alizon, M. 1985. Nucleotide sequence of AIDS virus LAV. Cell 40:9–17.
34. Weiss, R. A. 1988. Receptor molecule block HIV. Nature 331:15.
35. Wiley, D. C., Skehel, J., and Waterfield, M. 1977. Evidence from studies with a cross-linking reagent that the hemagglutinin of influenza virus is a trimer. Virology 79:446–448.
36. Wilson, L. A., Skehel, J., and Wiley, D. C. 1981. Structure of hemagglutinin membrane glycoprotein of influenza virus at 3A° resolution. Nature 289:366–373.

What is claimed is:

1. An isolated immune complex comprising a protein and an antibody that binds with said protein, wherein the protein is selected from the group consisting of gp80 of HIV-2 and gp65 of SIV, wherein said gp80 is a glycoprotein having an apparent molecular weight of 80 kDa, as determined by SDS-PAGE, and further wherein said gp65 is a glycoprotein having an apparent molecular weight of 65 kDa, as determined by SDS-PAGE.

2. The immune complex of claim 1, wherein the antibody, protein, or both the antibody and protein, are labeled with an immunoassay label selected from the group consisting of radioisotopes, enzymes, fluorescent labels, chemiluminescent labels, and chromophore labels.

3. An isolated immune complex comprising a peptide and an antibody that binds with said peptide, wherein the peptide has the following sequence:

VTAIEKYLQDQARLNSWGCAFRQVCH.

4. The immune complex of claim 3, wherein the antibody, peptide, or both the antibody and peptide, are labeled with an immunoassay label selected from the group consisting of radioisotopes, enzymes, fluorescent labels, chemiluminescent labels, and chromophore labels.

5. An immunogenic composition comprising an amount of gp80 protein of human immunodeficiency virus type 2 (HIV-2) sufficient to induce an immune response and a pharmaceutically acceptable carrier.

6. The immunogenic composition of claim 5 further comprising one or more proteins of HIV-2 selected from the group consisting of gp125, gp140, and gp300 of HIV-2.

7. A composition comprising at least one antigen selected from the group consisting of gp80 protein of HIV-2 and gp65 of SIV.

8. The composition of claim 7, further comprising one or more proteins selected from the group consisting of gp125, gp140, and gp300 of HIV-2.

* * * * *